(12) United States Patent
Garudadri et al.

(10) Patent No.: US 10,045,293 B2
(45) Date of Patent: Aug. 7, 2018

(54) METHOD AND APPARATUS FOR DISTRIBUTED PROCESSING FOR WIRELESS SENSORS

(71) Applicant: QUALCOMM Incorporated, San Diego, CA (US)

(72) Inventors: Harinath Garudadri, San Diego, CA (US); Pawan Kumar Baheti, Bangalore (IN); Somdeb Majumdar, Mission Viejo, CA (US)

(73) Assignee: QUALCOMM Incorporated, San Diego, CA (US)

( * ) Notice: Subject to any disclaimer, the term of this patent is extended or adjusted under 35 U.S.C. 154(b) by 12 days.

(21) Appl. No.: 15/288,809

(22) Filed: Oct. 7, 2016

(65) Prior Publication Data

US 2017/0099634 A1 Apr. 6, 2017

Related U.S. Application Data

(63) Continuation of application No. 12/777,698, filed on May 11, 2010, now abandoned.
(Continued)

(51) Int. Cl.
*G08C 17/00* (2006.01)
*H04W 52/02* (2009.01)
(Continued)

(52) U.S. Cl.
CPC ....... *H04W 52/0209* (2013.01); *A61B 5/0024* (2013.01); *H04J 3/0658* (2013.01);
(Continued)

(58) Field of Classification Search
USPC .................. 370/252, 254, 350, 428, 503–514
See application file for complete search history.

(56) References Cited

U.S. PATENT DOCUMENTS 5,448,202 A 9/1995 Owen
5,654,991 A * 8/1997 Andren ............. H04B 1/70755
375/355
(Continued)

FOREIGN PATENT DOCUMENTS

CN 101061481 A 10/2007
EP 1746427 A1 1/2007
(Continued)

OTHER PUBLICATIONS

Baheti P. K., et al., "An Ultra Low Power Pulse Oximeter Sensor Based on Compressed Sensing" Wearable and Implantable Body Sensor Networks, 2009. BSN 2009. Sixth International Workshop On, IEEE, Piscataway, NJ, USA, Jun. 3, 2009 (Jun. 3, 2009), pp. 144-148, XP031522335.
(Continued)

*Primary Examiner* — Yemane Mesfin
*Assistant Examiner* — Mon Cheri Davenport
(74) *Attorney, Agent, or Firm* — Patterson & Sheridan, L.L.P.

(57) ABSTRACT

Certain aspects of the present disclosure relate to a method for compressed sensing (CS). The CS is a signal processing concept wherein significantly fewer sensor measurements than that suggested by Shannon/Nyquist sampling theorem can be used to recover signals with arbitrarily fine resolution. In this disclosure, the CS framework is applied for sensor signal processing in order to support low power robust sensors and reliable communication in Body Area Networks (BANs) for healthcare and fitness applications.

18 Claims, 24 Drawing Sheets

Related U.S. Application Data

(60) Provisional application No. 61/266,324, filed on Dec. 3, 2009.

(51) Int. Cl.
   | | | |
   |---|---|---|
   | *H04J 3/06* | (2006.01) | |
   | *H04W 4/00* | (2018.01) | |
   | *A61B 5/00* | (2006.01) | |
   | *H04W 4/70* | (2018.01) | |

(52) U.S. Cl.
   CPC ............. *H04W 4/005* (2013.01); *H04W 4/70* (2018.02); *A61B 2560/0209* (2013.01)

(56) References Cited

U.S. PATENT DOCUMENTS

| | | | |
|---|---|---|---|
| 5,921,938 | A | 7/1999 | Aoyama et al. |
| 6,477,553 | B1 | 11/2002 | Druck |
| 7,266,306 | B1 | 9/2007 | Harley et al. |
| 7,289,049 | B1 | 10/2007 | Fudge et al. |
| 8,406,794 | B2 | 3/2013 | Lee et al. |
| 8,917,798 | B2 | 12/2014 | Garudadri et al. |
| 2004/0170154 | A1 | 9/2004 | Carter et al. |
| 2006/0155495 | A1* | 7/2006 | Osorio .................. A61B 5/0006 702/89 |
| 2007/0055151 | A1 | 3/2007 | Shertukde et al. |
| 2007/0086544 | A1* | 4/2007 | Fudge .................. H04B 1/0003 375/316 |
| 2007/0213619 | A1 | 9/2007 | Linder |
| 2007/0219823 | A1 | 9/2007 | Warner |
| 2008/0204298 | A1 | 8/2008 | Yamaji et al. |
| 2008/0281168 | A1 | 11/2008 | Gibson et al. |
| 2009/0081951 | A1 | 3/2009 | Erdmann et al. |
| 2009/0256973 | A1 | 10/2009 | Bazzani et al. |
| 2010/0063367 | A1 | 3/2010 | Friedman et al. |
| 2010/0082302 | A1 | 4/2010 | Garudadri et al. |
| 2010/0097259 | A1 | 4/2010 | Zhang |
| 2010/0246651 | A1 | 9/2010 | Baheti et al. |
| 2010/0272074 | A1 | 10/2010 | Cheng et al. |
| 2011/0134906 | A1 | 6/2011 | Garudadri et al. |
| 2011/0136536 | A1 | 6/2011 | Garudadri et al. |
| 2012/0263082 | A1 | 10/2012 | Garudadri et al. |

FOREIGN PATENT DOCUMENTS

| | | |
|---|---|---|
| JP | H05276147 A | 10/1993 |
| JP | 10011689 | 1/1998 |
| JP | 2002118541 A | 4/2002 |
| JP | 2006074326 A | 3/2006 |
| JP | 2008522459 A | 6/2008 |
| JP | 2009535934 A | 10/2009 |
| JP | 2012504022 | 2/2012 |
| WO | WO-2006054190 A1 | 5/2006 |
| WO | WO-2007127888 A2 | 11/2007 |
| WO | WO-2010036894 | 4/2010 |
| WO | WO-2010120513 | 10/2010 |

OTHER PUBLICATIONS

Baskiyar S, "A real-time fault tolerant intra-body network", Local Computer Networks, 2002. Proceedings. LCN 2002. 27th Annual IEEE Conference on Nov. 6-8, 2002, Piscataway, NJ, USA,IEEE, Nov. 6, 2002 (Nov. 6, 2002), pp. 235-240, XP010628172, ISBN: 978-0-7695-1591-5.

Harinath Garudadri, et al., "Packet loss mitigation for biomedical signals in healthcare telemetry", Engineering in Medicine and Biology Society, 2009, EMBC, Annual International Conference of the IEEE, IEEE, Piscataway, NJ, USA, Sep. 3, 2009 (Sep. 3, 2009), pp. 2450-2453, XP031566705, ISBN: 978-1-4244-3296-7.

Huang B Y, et al., "A pilot study on low power pulse rate detection based on compressive sampling", Engineering in Medicine and Biology Society, 2009. EMBC 2009. Annual International Conference of the IEEE, IEEE, Piscataway, NJ, USA, Sep. 3, 2009 (Sep. 3, 2009), pp. 753-756, XP031565453, ISBN: 978-1-4244-3296-7.

International Preliminary Report on Patentability—PCT/US2010/058763, The International Bureau of WIPO—Geneva, Switzerland, Feb. 16, 2012.

International Preliminary Report on Patentability—PCT/US2010/058766, The International Bureau of WIPO—Geneva, Switzerland—Mar. 13, 2012.

International Search Report and Written Opinion—PCT/US2010/058763, International Search Authority—European Patent Office—Apr. 4, 2011.

International Search Report and Written Opinion—PCT/US2010/058766, International Search Authority—European Patent Office—Mar. 31, 2011.

Javier Espina, et al., "Wireless Body Sensor Network for Continuous Cuff-less Blood Pressure Monitoring", Medical Devices and Biosensors, 2006, 3rd IEEE/EMBS International SUMM ER School On, IEEE, PI , Sep. 1, 2006 (Sep. 1, 2006), pp. 11-15, XP031088144, ISBN: 978-0-7803-9786-6.

Li-Qiong Y., et al., "Verilog design and research of finite state machine (FSM)," Microelectronics and Computer, 2004, vol. 21, No. 11, pp. 146-148 and p. 157, Abstract.

Otto, C., et al., "System Architecture of WBAN for Ubiquitous Health Monitoring", www.google.scholar.com Journal of Mobile Multimedia, vol. 1, No. 4 Jan. 15, 2006 (Jan. 15, 2006), pp. 307-326, XP002629701, Paramus, NJ 07652,USA Retrieved from the Internet: URL:http://www.cis.uoguelph.ca/{denko/Body Areal.pdf [retrieved on Mar. 21, 2011].

Rieger R, et al., "A Signal Based Clocking Scheme for A/D Converters in Body Sensor Networks", TENCON, 2006, IEEE Region 10 Conference, IEEE, PI, Nov. 14, 2006 (Nov. 14, 2006), pp. 1-4, XP031333192, ISBN: 978-1-4244-0548-0.

\* cited by examiner

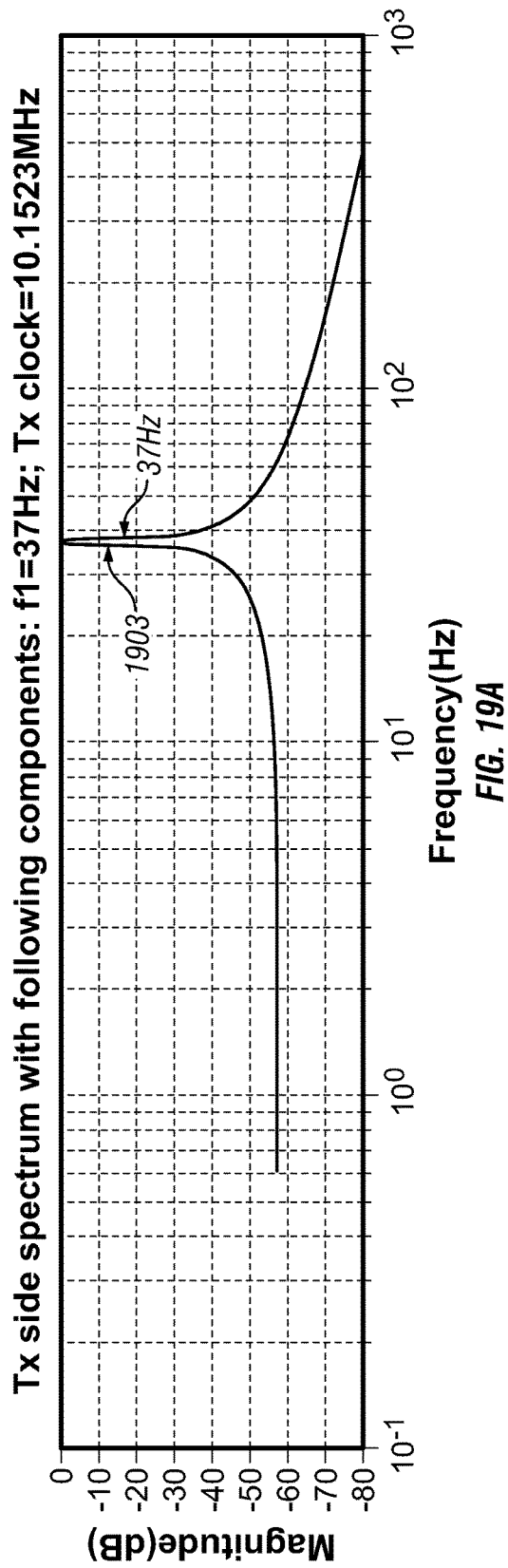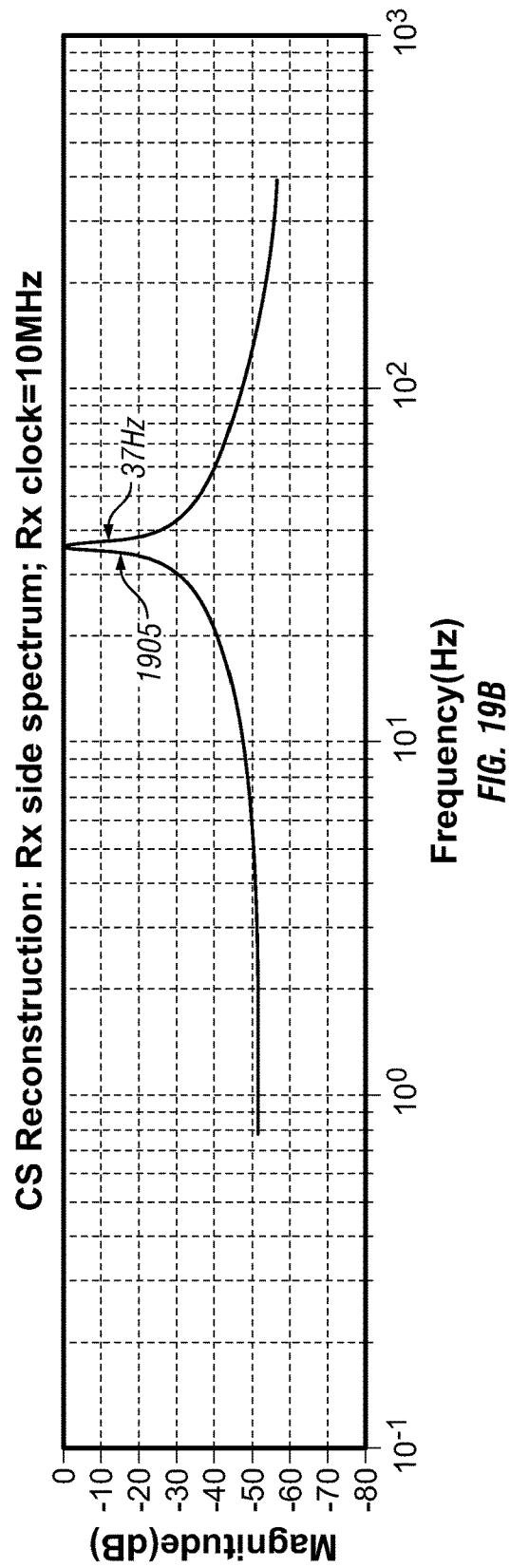

METHOD AND APPARATUS FOR DISTRIBUTED PROCESSING FOR WIRELESS SENSORS

CLAIM OF PRIORITY

The present application for patent is a continuation application of, and claims the benefit of priority from, U.S. patent application Ser. No. 12/777,698 filed on May 11, 2010, which in turn claims priority to Provisional Application No. 61/266,324, filed on Dec. 3, 2009, both applications being assigned to the assignee hereof and expressly incorporated herein by reference.

CROSS-REFERENCE TO RELATED APPLICATIONS

The present application is related to U.S. patent application Ser. No. 12/777,740, filed concurrently with U.S. patent application Ser. No. 12/777,698, and entitled METHOD AND APPARATUS FOR DISTRIBUTED PROCESSING FOR WIRELESS SENSORS, and U.S. patent application Ser. No. 13/532,078 filed on Jun. 25, 2012 and entitled METHOD AND APPARATUS FOR DISTRIBUTED PROCESSING FOR WIRELESS SENSORS, which is a divisional application of U.S. patent application Ser. No. 12/777,740, both applications being assigned to the assignee hereof and expressly incorporated herein by reference.

BACKGROUND

Field

Certain aspects of the present disclosure generally relate to signal processing and, more particularly, to a method for distributed processing for wireless sensors.

Description of Related Technology

Networks such as body area networks (BANs) make use of wireless sensors such as pulse oximeters to monitor vital signs of individuals. In order to improve the performance of such BANs, it is desirable to reduce the power consumption and complexity of such wireless sensors. Thus there is a need for low power sensors which can accurately detect and communicate information such as vital signs of individuals.

SUMMARY

In one aspect, a method of processing data is provided. The method includes maintaining, at a first apparatus, a first clock signal, transmitting, from the first apparatus, a clock synchronization signal for synchronizing a second clock signal, at a second apparatus, to the first clock signal, receiving, at the first apparatus, one or more packets comprising a first set of samples indicative of an input over a period of time, the first set of samples corresponding to the second clock signal, and generating, at the first apparatus, a second set of samples based, at least in part, on the first set of samples, wherein the second set of samples corresponds to the first clock signal.

In another aspect, an apparatus for processing data is provided. The apparatus includes a processing system, configured to maintain a first clock signal, a transmitter configured to transmit a clock synchronization signal for synchronizing a second clock signal to the first clock signal, and a receiver configured to receive one or more packets comprising a first set of samples indicative of an input over a period of time, the first set of samples corresponding the second clock signal. The processing system is further configured to generate a second set of samples based, at least in part, on the first set of samples, the second set of samples corresponding to the first clock signal.

Another aspect provides an apparatus for processing data. The apparatus includes means for maintaining a first clock signal, means for transmitting a clock synchronization signal for synchronizing a second clock signal to the first clock signal, means for receiving one or more packets comprising a first set of samples indicative of an input over a period of time, the first set of samples corresponding the second clock signal, and means for generating a second set of samples based, at least in part, on the first set of samples, the second set of samples corresponding to the first clock signal.

Another aspect provides a computer program product. The computer program product includes a computer-readable medium. The computer-readable medium includes computer executable instructions that, if executed by an apparatus, cause the apparatus to perform a method. The method includes maintaining, a first clock signal, transmitting a clock synchronization signal for synchronizing a second clock signal to the first clock signal, receiving one or more packets comprising a first set of samples indicative of an input over a period of time, the first set of samples corresponding to the second clock signal, and generating a second set of samples based, at least in part, on the first set of samples, wherein the second set of samples corresponds to the first clock signal.

Another aspect provides a mobile phone. The mobile phone includes an antenna, a processing system configured to maintain a first clock signal, a transmitter configured to transmit, via the antenna, a clock synchronization signal for synchronizing a second clock signal to the first clock signal, and a receiver configured to receive, via the antenna, one or more packets comprising a first set of samples indicative of an input over a period of time, the first set of samples corresponding the second clock signal. The processing system is further configured to generate a second set of samples based, at least in part, on the first set of samples, the second set of samples corresponding to the first clock signal.

Another aspect provides a method of data communication. The method includes receiving a clock synchronization signal, adjusting a clock signal based, at least in part, on the clock synchronization signal, generating a first set of samples corresponding to the adjusted clock signal, generating one or more packets comprising, at least in part, the first set of samples, and transmitting the one or more packets.

Another aspect provides an apparatus for data communication. The apparatus includes a receiver configured to receive a clock synchronization signal, a processing system configured to adjust a clock signal based, at least in part, on the clock synchronization signal, generate a first set of samples corresponding to the adjusted clock signal, and generate one or more packets comprising, at least in part, the first set of samples, and a transmitter configured to transmit the one or more packets.

Another aspect provides an apparatus for data communication. The apparatus includes means for receiving a clock synchronization signal, means for adjusting a clock signal based, at least in part, on the clock synchronization signal, means for generating a first set of samples corresponding to the adjusted clock signal, means for generating one or more packets comprising, at least in part, the first set of samples, and means for transmitting the one or more packets.

Another aspect provides a computer program product. The computer program product includes a computer-readable medium. The computer-readable medium includes computer executable instructions that, if executed by an apparatus, cause the apparatus to perform a method. The method includes receiving a clock synchronization signal, adjusting a clock signal based, at least in part, on the clock synchronization signal, generating a first set of samples corresponding to the adjusted clock signal, generating one or more packets comprising, at least in part, the first set of samples, and transmitting the one or more packets.

Another aspect provides a sensing device. The device includes a transducer configure to receive an input, a receiver configured to receive a clock synchronization signal, a processing system configured to adjust a clock signal based, at least in part, on the clock synchronization signal, generate a first set of samples corresponding to the adjusted clock signal based, at least in part, on the input, and generate one or more packets comprising, at least in part, the first set of samples, and a transmitter configured to transmit the one or more packets.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

FIG. 19A-C illustrate waveforms depicting the effect of a clock mismatch between a transmitter and receiver with transmitter clock rate higher than receiver clock rate in accordance with certain aspects of the present disclosure.

DETAILED DESCRIPTION

Figure 1:
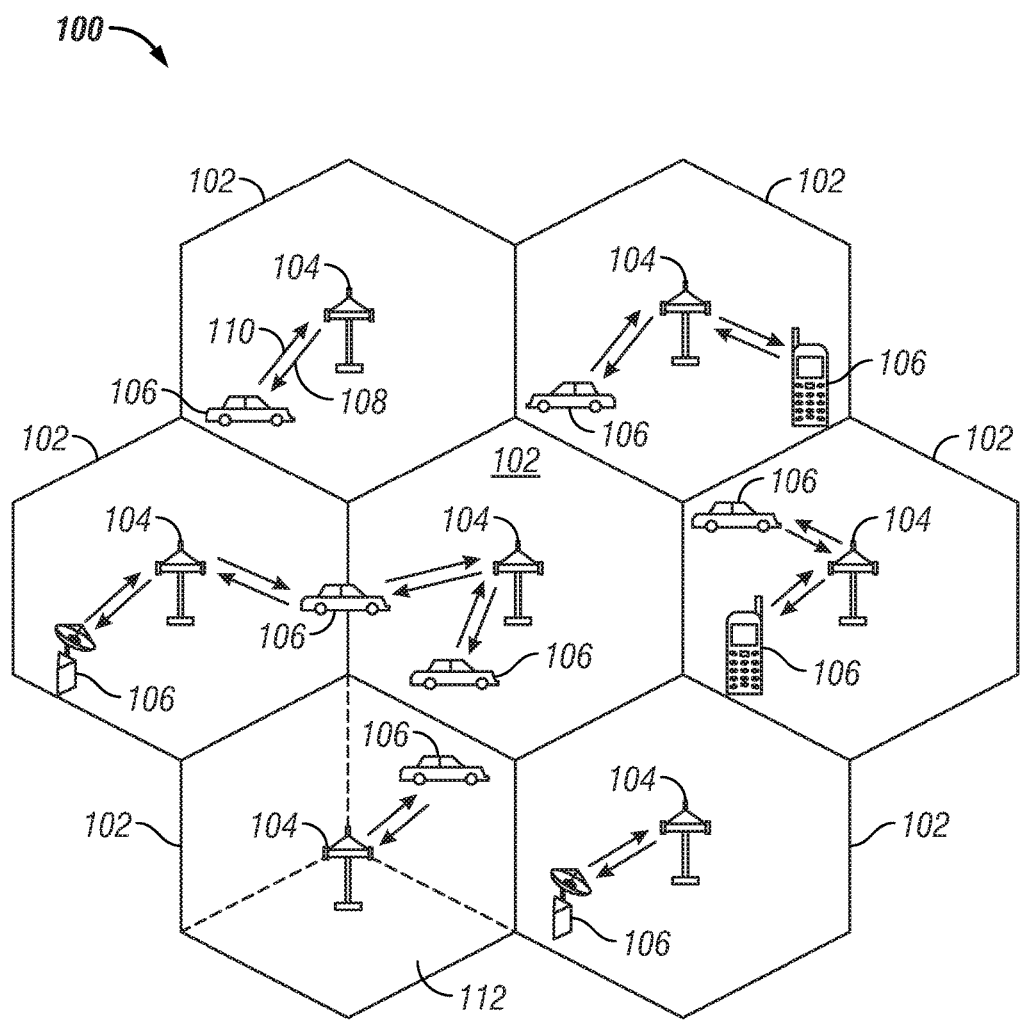
FIG. 1 illustrates an example wireless communication system.

Various aspects of the novel systems, apparatus and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that that the scope of the disclosure is intended to cover any aspect of the novel systems, apparatus, and methods disclosed herein, whether implemented independently of or combined with any other aspect of the invention. For example, an apparatus may be implemented or a method may be practiced using any number of the aspects set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different wireless technologies, system configurations, networks, and transmission protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

An Example Wireless Communication System

The teachings herein may be incorporated into (e.g., implemented within or performed by) a variety of wired or wireless apparatuses (e.g., nodes). In some aspects, a node implemented in accordance with the teachings herein may comprise an access point or an access terminal.

An access point ("AP") may comprise, be implemented as, or known as NodeB, Radio Network Controller ("RNC"), eNodeB, Base Station Controller ("BSC"), Base Transceiver Station ("BTS"), Base Station ("BS"), Transceiver Function ("TF"), Radio Router, Radio Transceiver, Basic Service Set ("BSS"), Extended Service Set ("ESS"), Radio Base Station ("RBS"), or some other terminology.

An access terminal ("AT") may comprise, be implemented as, or known as an access terminal, a subscriber station, a subscriber unit, a mobile station, a remote station, a remote terminal, a user terminal, a user agent, a user device, user equipment, or some other terminology. In some implementations an access terminal may comprise a cellular telephone, a cordless telephone, a Session Initiation Protocol ("SIP") phone, a wireless local loop ("WLL") station, a personal digital assistant ("PDA"), a handheld device having wireless connection capability, or some other suitable processing device connected to a wireless modem. Accordingly, one or more aspects taught herein may be incorporated into a phone (e.g., a cellular phone or smart phone), a computer (e.g., a laptop), a portable communication device, a portable computing device (e.g., a personal data assistant), an entertainment device (e.g., a music or video device, or a satellite radio), a global positioning system device, or any other suitable device that is configured to communicate via a wireless or wired medium. In some aspects the node is a wireless node. Such wireless node may provide, for example, connectivity for or to a network (e.g., a wide area network such as the Internet or a cellular network) via a wired or wireless communication link.

FIG. 1 illustrates an example of a wireless communication system 100 in which aspects of the present disclosure may be employed. The wireless communication system 100 may be a broadband wireless communication system. The wireless communication system 100 may provide communication for a number of cells 102, each of which is serviced by a base station 104. A base station 104 may be a fixed station that communicates with user terminals 106. The base station 104 may alternatively be referred to as an access point, a Node B or some other terminology.

FIG. 1 depicts various user terminals 106 dispersed throughout the system 100. The user terminals 106 may be fixed (i.e., stationary) or mobile. The user terminals 106 may alternatively be referred to as remote stations, access terminals, terminals, subscriber units, mobile stations, stations, user equipment, etc. The user terminals 106 may be wireless devices, such as cellular phones, personal digital assistants (PDAs), handheld devices, wireless modems, laptop computers, personal computers, etc.

A variety of processes and methods may be used for transmissions in the wireless communication system 100 between the base stations 104 and the user terminals 106. For example, signals may be sent and received between the base stations 104 and the user terminals 106 in accordance with OFDM/OFDMA techniques. If this is the case, the wireless communication system 100 may be referred to as an OFDM/OFDMA system. Alternatively, signals may be sent and received between the base stations 104 and the user terminals 106 in accordance with CDMA technique. If this is the case, the wireless communication system 100 may be referred to as a CDMA system.

A communication link that facilitates transmission from a base station 104 to a user terminal 106 may be referred to as a downlink (DL) 108, and a communication link that facilitates transmission from a user terminal 106 to a base station 104 may be referred to as an uplink (UL) 110. Alternatively, a downlink 108 may be referred to as a forward link or a forward channel, and an uplink 110 may be referred to as a reverse link or a reverse channel.

A cell 102 may be divided into multiple sectors 112. A sector 112 is a physical coverage area within a cell 102. Base stations 104 within a wireless communication system 100 may utilize antennas that concentrate the flow of power within a particular sector 112 of the cell 102. Such antennas may be referred to as directional antennas.

Figure 2:
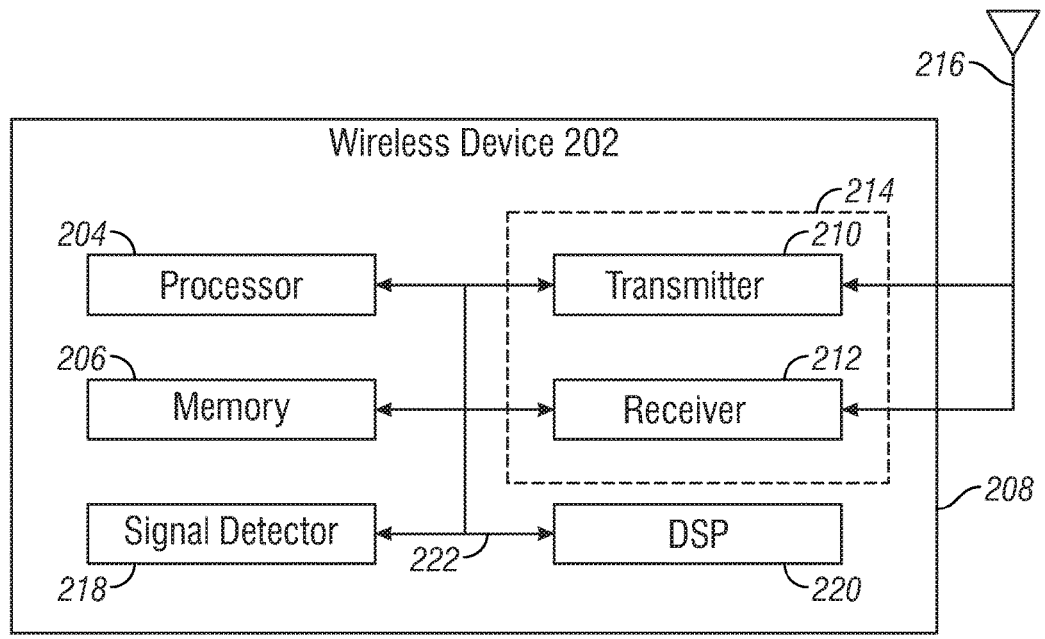
FIG. 2 is a block diagram illustrating various components that may be utilized in a wireless device.

FIG. 2 illustrates various components that may be utilized in a wireless device 202 that may be employed within the wireless communication system 100. The wireless device 202 is an example of a device that may be configured to implement the various methods described herein. The wireless device 202 may be a base station 104 or a user terminal 106.

The wireless device 202 may include a processor 204 which controls operation of the wireless device 202. The processor 204 may also be referred to as a central processing unit (CPU). Memory 206, which may include both read-only memory (ROM) and random access memory (RAM), provides instructions and data to the processor 204. A portion of the memory 206 may also include non-volatile random access memory (NVRAM). The processor 204 typically performs logical and arithmetic operations based on program instructions stored within the memory 206. The instructions in the memory 206 may be executable to implement the methods described herein. Further, the functionality of processor 204 and the DSP 220 may be included in a single module.

The wireless device 202 may also include a housing 208 that may include a transmitter 210 and a receiver 212 to allow transmission and reception of data between the wireless device 202 and a remote location. The transmitter 210 and receiver 212 may be combined into a transceiver 214. An antenna 216 may be attached to the housing 208 and electrically coupled to the transceiver 214. The wireless device 202 may also include (not shown) multiple transmitters, multiple receivers, multiple transceivers, and/or multiple antennas.

The wireless device 202 may also include a signal detector 218 that may be used in an effort to detect and quantify the level of signals received by the transceiver 214. The signal detector 218 may detect such signals as total energy, energy per subcarrier per symbol, power spectral density and other signals. The wireless device 202 may also include a digital signal processor (DSP) 220 for use in processing signals. The signal detector may also be connected to a transducer such as a microphone, ECG electrodes, photodiodes, etc (not shown).

The various components of the wireless device 202 may be coupled together by a bus system 222, which may include a power bus, a control signal bus, and a status signal bus in addition to a data bus.

Body Area Network Concept

Figure 4:
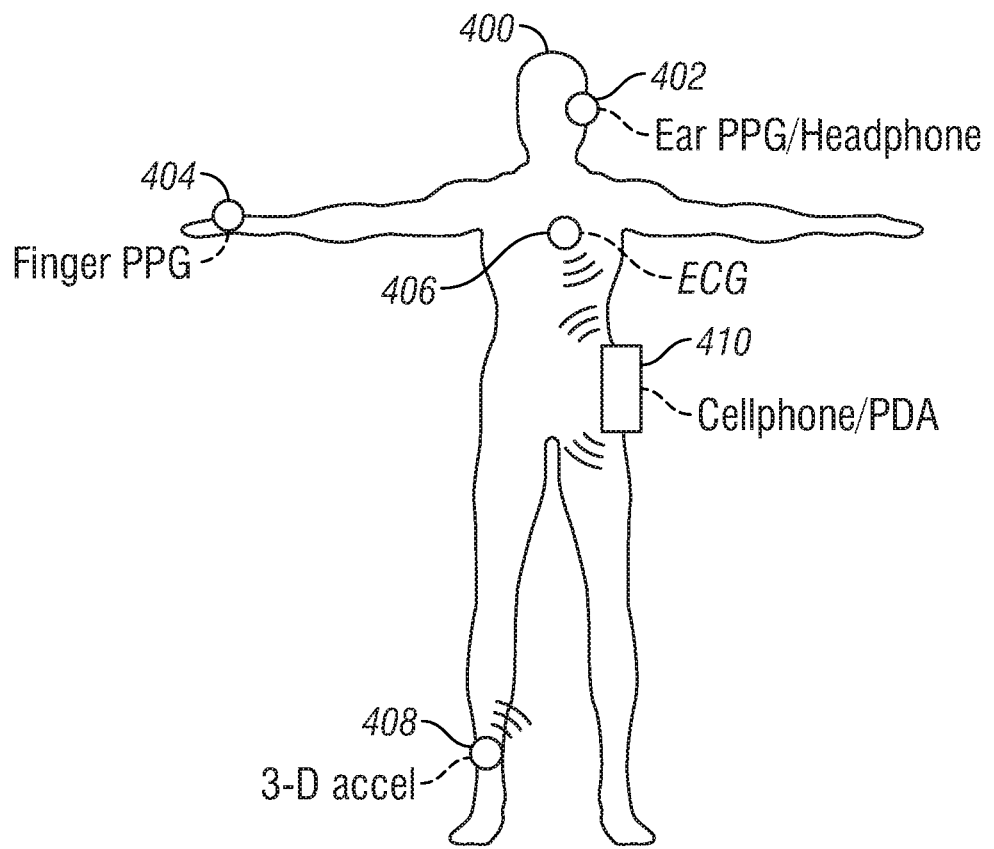
FIG. 4 illustrates an example of a body area network (BAN).

FIG. 4 illustrates an example of a body area network (BAN) 400. Body area networks represent a promising concept for healthcare applications such as continuous monitoring of vital signs for diagnostic purposes, effects of medicines on chronic ailments, etc.

Figure 5:
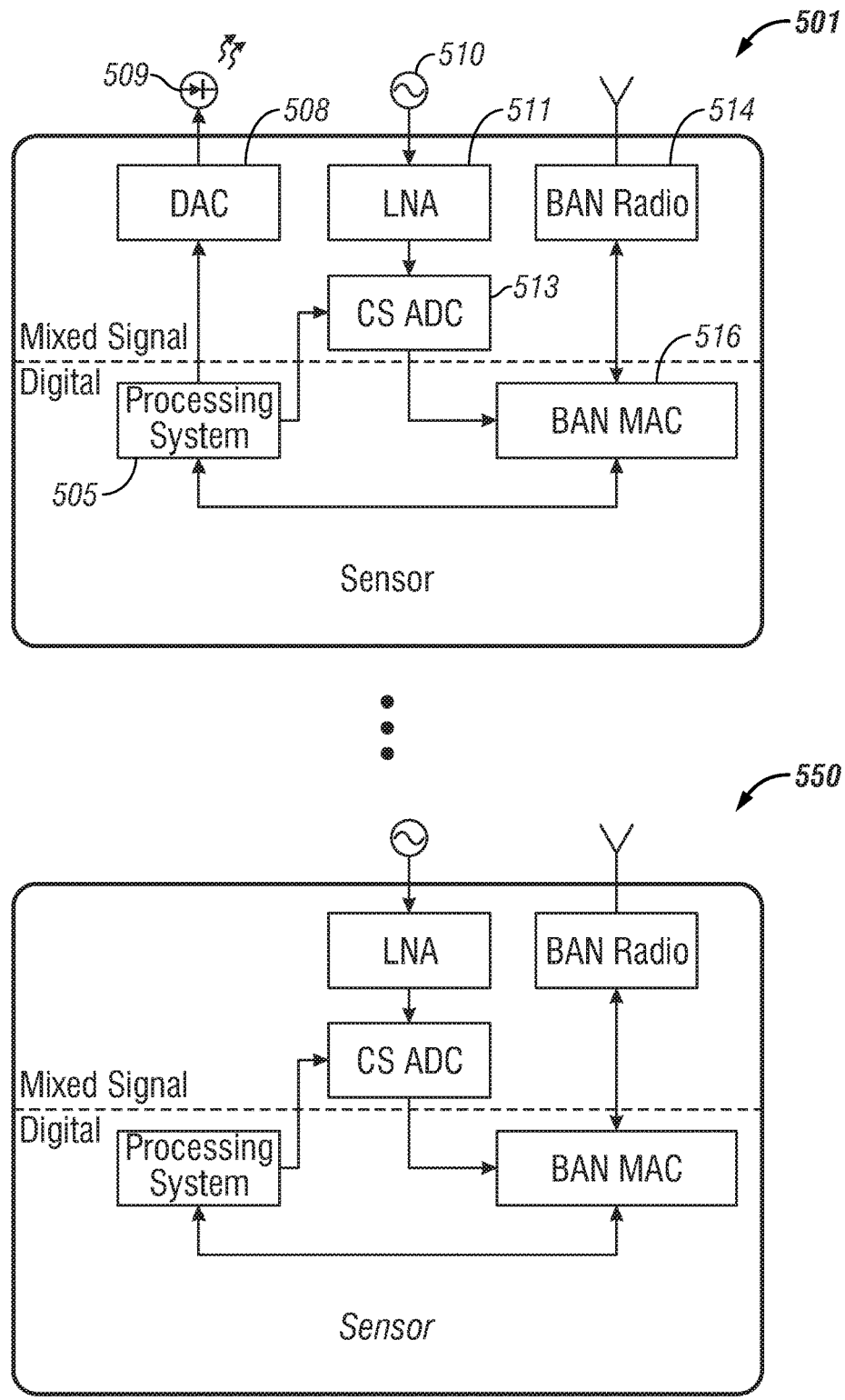
FIG. 5 is a block diagram illustrating an array of sensors used within the BAN.

The BAN may consist of several acquisition circuits. Each acquisition circuit may comprise wireless sensor that senses one or more vital signs and communicates them to an aggregator (i.e., an access terminal) such as a mobile handset, a wireless watch, or a Personal Data Assistant (PDA). The aggregator is sometimes referred to as the gateway. Sensors 402, 404, 406, and 408 that acquire various biomedical signals and transmit them over a wireless channel to an aggregator 410 may have the same functionality as access points 104. FIG. 5 illustrates detailed block diagram of an array of biomedical sensors 501 and 550 that may correspond to sensors 402-408 within the BAN 400.

Figure 6:
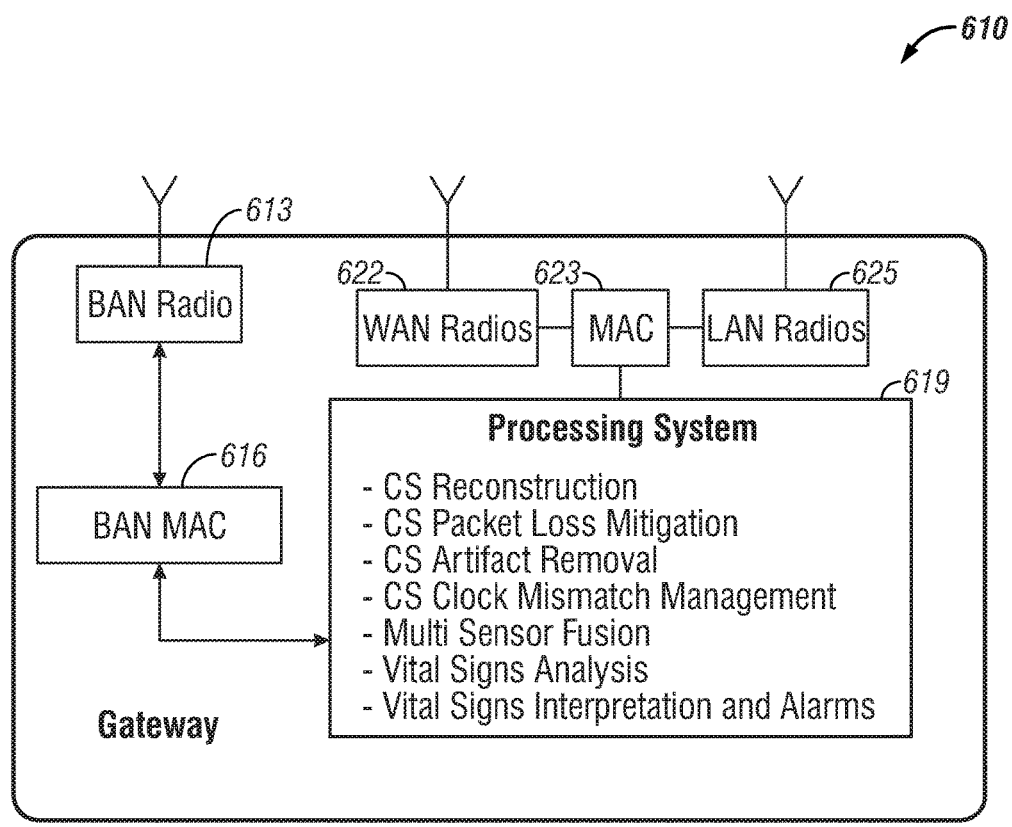
FIG. 6 is a block diagram illustrating an aggregator used within the BAN.

The aggregator 410 illustrated in FIG. 4 may receive and process various biomedical signals transmitted over a wireless channel from sensors 402-408. The aggregator 410 may be a mobile handset or a PDA, and may have the same functionality as a mobile device 106 from FIG. 1. In other embodiments, the aggregator 410 may be an access point or femto node. FIG. 6 illustrates a detailed block diagram of an aggregator 610 that may correspond to the aggregator 410 within the BAN 400. The aggregator 610 may be an example of the receiver 212 from FIG. 2.

It may be desirable for sensors used in the BAN to be non-intrusive and long lasting. Photoplethysmograph (PPG) and Electro Cardiogram (ECG) signals may be considered in this disclosure to demonstrate benefits of compressed sensing (CS) techniques for sensor signal processing. The PPG, the ECG and the activity sensing cover a large percentage of chronic ailments in a large segment of human population, and thus provide significant opportunities for wireless technologies in the BAN and mobile devices with wireless area network (WAN) connectivity to improve diagnosis and care of such ailments.

Figure 7:
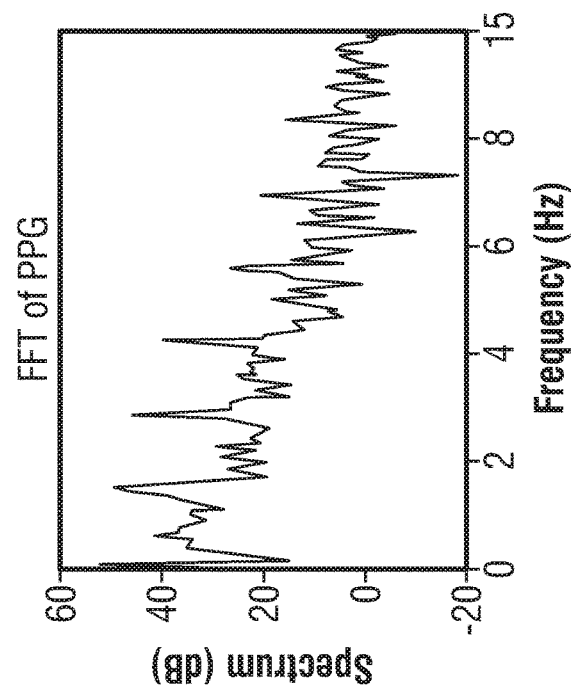
FIG. 7 illustrates an example of a time-domain photoplethysmograph (PPG) signal and its frequency spectrum.
Figure 7:
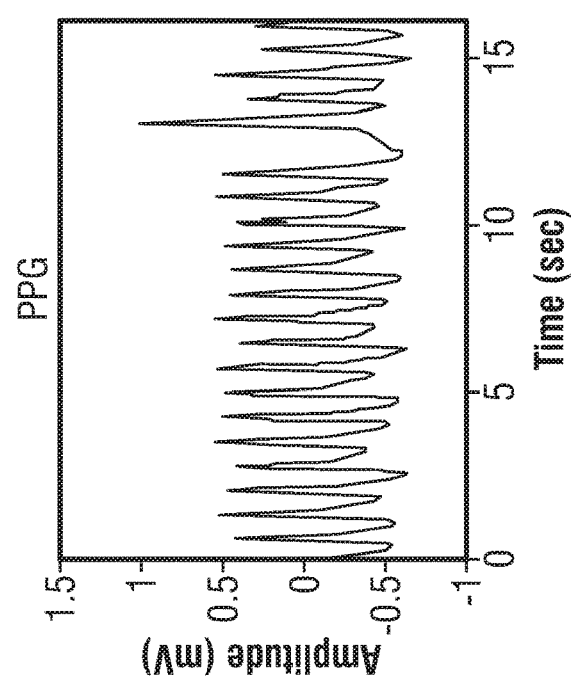

Pulse oximeter sensors can generate the PPG waveform which may enable continuous monitoring of blood oxygenation (also called $S_pO_2$), a crucial indicator of pulmonary system including lungs and respiration. A blood carries oxygen, nutrients and chemicals to the body cells in order to ensure their survival, proper functioning and to remove the cellular wastes. $S_pO_2$ is extensively used in clinical settings for diagnosis, surgery, long term monitoring, etc. FIG. 7 illustrates an example of a time-domain PPG signal and its frequency spectrum.

Figure 8:
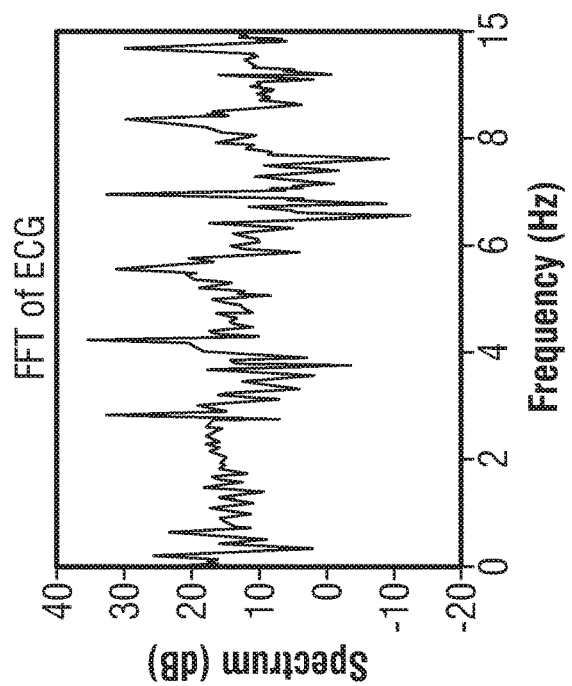
FIG. 8 illustrates an example of a time-domain electrocardiogram (ECG) signal and its frequency spectrum.
Figure 8:
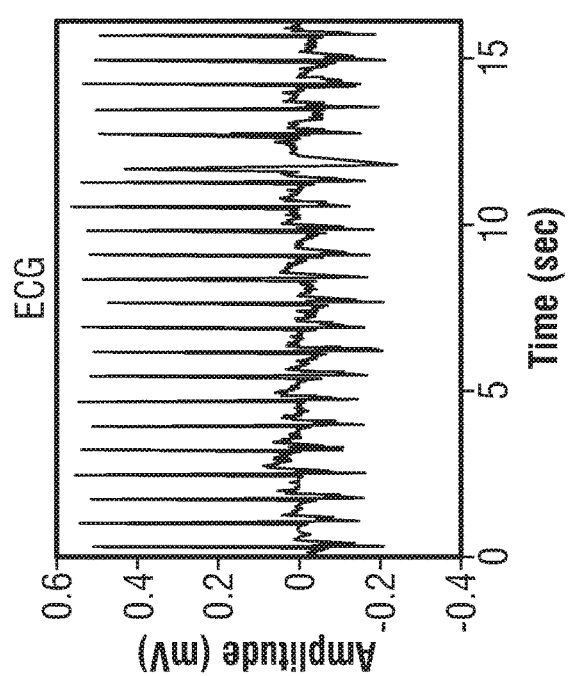

The ECG is another important vital sign for assessing the cardiovascular system. Heart is one of the most hard working body parts, pumping about six liters of blood per minute through the body in humans. Electrical signals generated during each cardiac cycle form the ECG signal and can be easily captured by Ag/AgCl electrode sensors. The ECG may be routinely used in clinical settings for diagnosing heart related problems and continuous monitoring of the ECG may enable early diagnosis of many chronic conditions. FIG. 8 illustrates an example of a time-domain ECG signal and its frequency spectrum. A blood pressure (BP) is another vital sign with enormous clinical value. A systolic blood pressure (SBP) and a diastolic blood pressure (DBP) may be estimated using the ECG and the PPG signals.

In certain aspects, the sensors and gateways described herein make use of compressed sensing (CS). In CS, significantly fewer sensor measurements than that suggested by Shannon/Nyquist sampling theorem can be used to recover signals with arbitrarily fine resolution. This is possible when the signals being sensed are inherently compressible or sparse in certain domain. A class of band-limited signals with M non-zero spectral components is considered, where $M \ll f_s/2$ and $f_s$ is a suggested sampling rate, such as the Nyquist sampling rate. Traditionally, such signals can be compressed after acquisition for more efficient transmission and/or storage.

In the CS framework, the acquisition process (i.e., sensing) can be integral to source compression and can be independent of the sparse nature of the signals. However, this sparsity information may be required at a receiver side in order to perform signal reconstruction. Measurements in the CS framework are generally defined as inner products of the signal with random basis functions. These signals can be accurately recovered if at least M log(N/M) samples are available at the receiver, where N is the number of samples in the reconstruction, albeit with some additional computational complexity at the receiver. This can be useful in the context of a body area network (BAN) as the computational complexity is shifted to nodes with flexible power budget in order to increase working life of sensors employed in the BAN.

The CS paradigm can be used for applications concerning signal detection/classification, imaging, data compression and Magnetic Resonance Imaging (MRI). Benefits of the CS are reported in terms of improved signal fidelity and superior recognition performance In the present disclosure, the CS-based signal processing is proposed for providing low power sensors within the BAN for healthcare and fitness applications.

One aspect of the BAN in healthcare applications is to provide a reliable communication link between sensors (i.e., transmitters) and an aggregator (i.e., a receiver), while minimizing sensor power and communication latency.

FIG. 5 illustrates an example block diagram of array of sensors used within the BAN in accordance with certain aspects of the present disclosure. In one aspect, sensors 501 and 550 are designed to take advantage of compressed sensing in order to significantly lower the power consumption and complexity of the circuitry used in the sensor. For example, the use of compressed sensing may allow the sensors 501 and 550 to omit certain processing steps and certain signal conditioning steps in order to decrease power consumption. The omission of these steps and the corresponding circuitry and functionality is described in greater detail below.

Sensor 501 comprises processing system 505. Processing system 505 may operate to control and direct the operation of sensor 501. In one aspect, processing system 505 includes clock circuitry for generating, maintaining, and adjusting a clock signal. As described herein, the reduced complexity of the operation of sensor 501 may allow processing system 505 to be simplified such that more power intensive hardware such as a CPU may not be necessary for the sensor 501 to perform its function. For example, a dedicated hardware finite state machine could be used instead. Processing system 505 is coupled to a digital-to-analog converter (DAC) 508. The DAC 508 is coupled to a transducer 509. The DAC 508 may be configured to drive the transducer 509 in order to generate signals to be measured by the sensor 501. For example, in one aspect, sensor 501 comprises a pulse oximeter sensor. The sensor 501 may use DAC 508 to convert an actuation signal from the processing system 505 in order to drive transducer 509, a light emitting diode (LED) in this aspect, for measurement purposes. In other aspects, sensors may not require actuation signals and may omit DAC 508 and the transducer 509. The sensor 501 may further comprise a transducer 510 for receiving an analog signal. As described above, the transducer 510 may comprise a light detector or other sense circuit. The transducer 510 is coupled to conditioning circuitry, such as, for example, low noise amplification (LNA) circuit 511. The LNA circuit 511 is coupled to a sampling circuit such as, for example, compressed sensing (CS) analog to digital converter (ADC) 513. In one aspect, the CS ADC 513 may be implemented, at least in part, as a sample and hold circuit (not shown) in line with a quantization circuit (not shown). The structure of CS ADC 513 according to various aspects is described in greater detail below with respect to FIG. 3. As described herein, the CS ADC 513 may be used to generate a set of samples representing the analog signal received by the transducer over a certain period of time. The sensor 501 may further comprise a media access controller 516 and radio 514. Processing system 505, in conjunction with MAC 516, may be configured to packetize the set of samples generated by the CS ADC 513 and to transmit one or more of such packets via the radio 514.

Figure 21A:
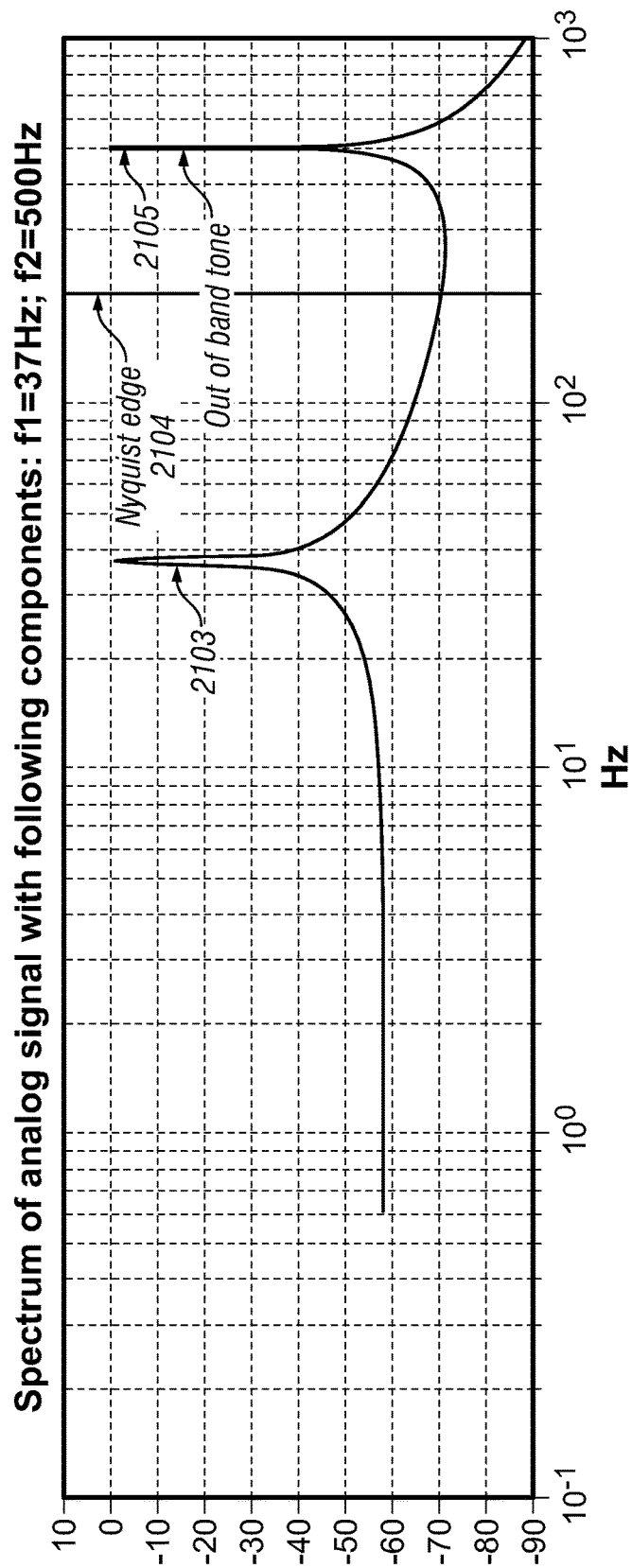
FIG. 21A-B illustrate waveforms depicting the effect of omitting a low pass filter under Nyquist sampling and compressed sensing regimes in accordance with certain aspects of the present disclosure.
Figure 21B:
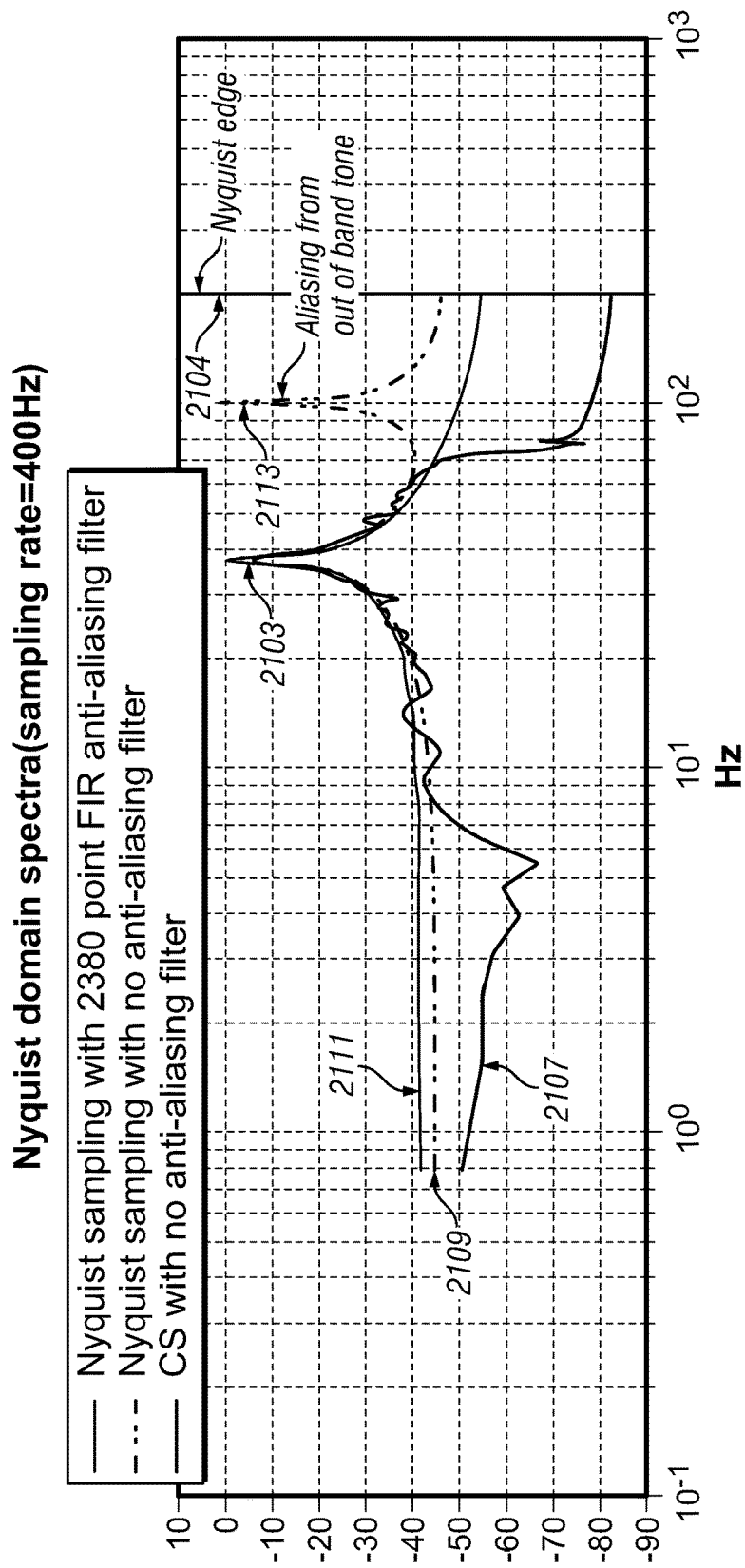

Advantageously, the reduced complexity of the operations at the sensor 501 enables the elimination of certain circuitry that would otherwise traditionally be used in sensors. For example, to perform sampling at the Nyquist rate, an anti-aliasing filter is traditionally used to prevent aliasing. Such filtering may require significant power consumption. By using CS techniques, the performance requirements of anti-aliasing circuitry may be relaxed. Alternatively, in some embodiments, the anti-aliasing circuitry may be omitted. This is illustrated with respect to FIGS. 21A and 21B. In FIG. 21A a Nyquist edge of 200 Hz is presented. FIG. 21A also illustrates a signal having a significant component 2103 below the Nyquist edge, at about 37 Hz and a significant component 2105 above the Nyquist edge at about 500 Hz. The component 2105 above the Nyquist edge is an out of band tone. Traditionally, a Nyquist edge of 200 Hz requires a Nyquist sampling frequency of 400 samples/second. Traditional Nyquist sampling requires an anti-aliasing filter to remove all components above 200 Hz and then sampling uniformly with 400 samples/second. The result of omitting the anti-aliasing filter but still using Nyquist reconstruction is illustrated in FIG. 21 B. In particular, waveform 2109 illustrates the spectrum of a digital signal uniformly sampled with 400 samples/second, but with no anti-aliasing filter. The aliasing effect of the 500 Hz component 2105 of FIG. 21A is illustrated by the spurious component 2113 at 100 Hz in FIG. 21B. Thus, as illustrated, the omission of an anti-aliasing filter while using traditional sampling techniques provides inadequate results. To contrast, waveform 2111 illustrates the result of traditional Nyquist sampling when using an anti-aliasing filter. As illustrated, the component 2103 at 37 Hz is preserved and no spurious tones are promulgated when traditional Nyquist sampling is combined with an anti-aliasing filter. Further, FIG. 21B illustrates a waveform 2107 showing a reconstruction using CS sampling without an anti-aliasing filter. As illustrated, the waveform 2107 recreates the component 2103 at 37 Hz but does not include any spurious tones from aliasing. In generating the CS reconstruction 2107, the average sampling rate was 400 samples/second, which is the same as that for the Nyquist cases. However, as describe above, the sampling in the CS reconstruction is non-uniform. Further, a priori information that spectral components greater than 100 Hz are out of band of interest may be utilized and out of band components may not be reconstructed.

In one aspect, additional sensors such as the sensor 550 may also be included in a body area network as described in FIG. 4. For example, sensor 501 may comprise a pulse oximeter while sensor 550 may comprise a three dimensional accelerometer. As described below, the output from the sensors 501 and 550 may be synthesized and otherwise processed by a common gateway.

The processing system 505 may be implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The processing system 505 may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system 505 to perform the various functions described herein.

Figure 3:
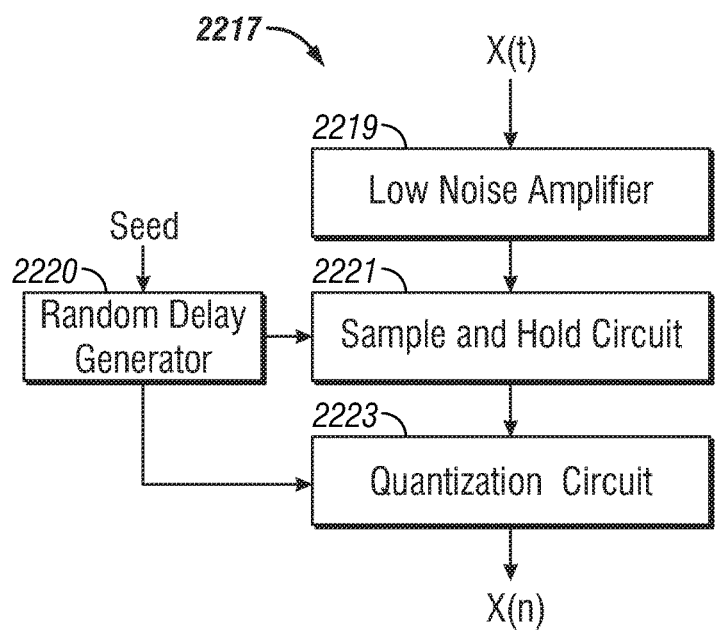
FIG. 3 is a block diagram of portions of a sensor in accordance with certain aspects of the present disclosure.

FIG. 3 illustrates a low noise amplifier (LNA) 2219, a random delay generator 2220, a sample and hold (S&H) circuit 2221, and a quantization circuit 2223. The LNA circuit 2219 may correspond to the LNA circuit 511 of FIG. 5. The random delay generator 2220, S&H circuit 2221 and quantization circuit 2223 may correspond to the CS ADC 513 of FIG. 5. As illustrated, an analog signal X(t) may be received at the LNA 2219. The analog signal may be processed sequentially by the LNA circuit, 2219, the S&H circuit 2221, and the quantization circuit 2223. The random delay generator 2220 may control the instances at which the signal is sampled by S&H circuit 2221 and sampled by quantization circuit 2223. The random delay generator 2220 may receive a seed as input for use in generating the non-uniform sampling instances. The output of the quantization circuit 2223 is a digital signal used advantageously in the manner described herein. In one aspect, each circuit is configured to provide an output directly to the next circuit without any intervening circuitry. Thus, as described above, in this aspect, no low pass or anti-aliasing filter is present or used. As described, this omission advantageously results in reduced power consumption, reduced complexity, and reduced cost for the sensor without compromising the quality of the data provided by the sensor.

FIG. 6 illustrates an aggregator 610. Aggregator 610 may also be referred to herein as a gateway 610. Gateway 610 may be used to receive data, such as sets of samples from sensor inputs, from one or more sensors such as sensors 501 and 550 of FIG. 5. Gateway 610 may be further configured to perform additional processing on the data as described herein. In one aspect, gateway 610 comprises a BAN radio 613. The BAN radio 613 may be configured to receive transmissions from sensors such as sensors 501 and 550 of FIG. 5. The BAN radio 613 may also be configured to transmit messages to one or more wireless sensors. For example, as described herein, gateway 610 may be configured to transmit requests for data or for clock synchronization to one or more wireless sensors via the BAN radio 613. Gateway 610 further comprises a media access controller (MAC) 616 coupled to the BAN radio 613 for controlling communications through the BAN radio 613. Gateway 610 further comprises a processing system 619 coupled to the MAC 616. The processing system 619 may be configured to communicate with the sensors via the MAC 616 and BAN radio 613. For example, as described herein, the processing system 619 may be configured to receive a set of CS samples from a sensor and to reconstruct a Nyquist set of samples from the received sample set. Similarly, the processing system 619 may mitigate packet loss, remove artifacts in the received sample set, determine and mitigate clock misalignment between the gateway 610 and the sensors, align samples sets from a plurality of sensors, and analyze the received or reconstructed samples to interpret vital signs and trigger alarms. In one aspect, processing system 619 includes clock circuitry for generating and maintaining a clock signal.

The gateway 610 may further comprise additional radios such as wide area network radios 622, e.g., a third generation radio, or LAN radios 625, e.g., WiFi radios. These radios may be used to communicate information from the sensors to other devices. For example, a person's cell phone may function as the gateway 610. The gateway 610 may further comprise another media access controller (MAC) 623 for controlling communication between the processing system 619 and the WAN and LAN radios 622 and 625. In some embodiments, the MAC's 616 and 623 may be implemented by shared hardware or software. After determining vital signs based on data from the sensors, the processing system 619 may transmit information about the vital signs to a remotely located physician via the WAN radios 622 of the LAN radios 625. Advantageously, the centralized processing of samples from the sensors at the gateway 610 facilitates lower power consumption and reduced complexity in the sensors. Further, the gateway 610 may act as a centralized clock synchronization controller for the plurality of sensors.

The processing system 619 may be implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The processing system 619 may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system 619 to perform the various functions described herein.

Figure 9:
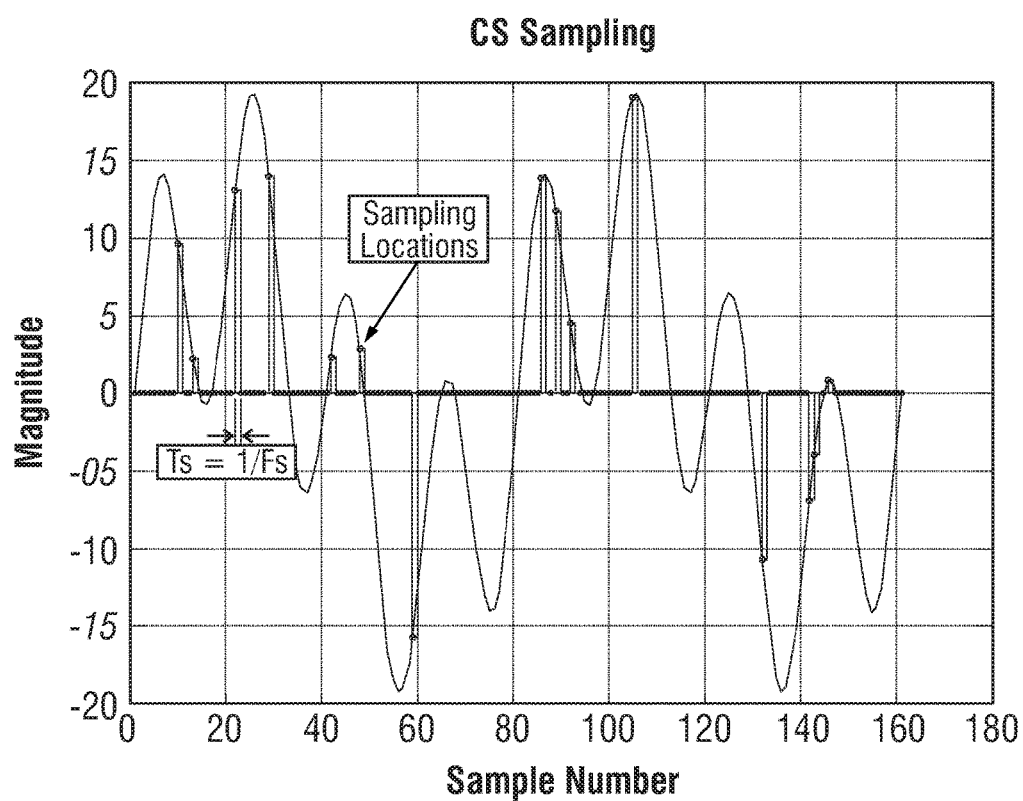
FIG. 9 illustrates a compressed sensing sample distribution.

FIG. 9 illustrates a compressed sensing sample distribution in accordance with certain aspects of the present disclosure. As described herein, for CS sampling, the following conditions may be met for the analog signal to be faithfully reconstructed from the digital signal. First, the hold time $T_h < \frac{1}{2} * f_{max}$, where $f_{max}$ is the maximum spectral component in a signal x(t) with a magnitude $\|X(f_{max})\| < 6*q$ dB, where q is the number of bits in quantizing x(n). Second, in any given time window, the number of measurements, k, in CS sampling shall be $c*M*\log(N/M)$, where M is the number of spectral components above 6*qdB and N is the number of Nyquist samples to be reconstructed in the given time window. The constant c may represent the coherence between the measurement basis and the sparse basis. For example, the more incoherent the two bases are, the smaller the value of c is. In certain aspects, c is selected so that k is approximately three to five times the value M. In some aspects c may have a value between 1 and 2. As can be seen in FIG. 9, the number of samples in the same time-window is much less than would be present for Nyquist rate sampling. In this example, an under-sampling ratio of 10 was used; this implies that on average, the number of samples used for a given time window for CS reconstruction is 1/10th that of traditional Nyquist sampling. Advantageously, using fewer samples reduces the power consumption at the sensor. Indeed, less processing is used to generate the samples. In addition, for such sensors as pulse oximeters, LEDs or similar elements may be powered for a reduced duration corresponding to the sampling periods for the signal. When x(t) is sparse in the spectral domain, k may be much less than $F_s$ measurements for every second of observation, depending on the redundancy in x(t). In addition, there may be significant power gains in the sensor from transferring analog circuit complexity at the sensor to digital domain reconstruction complexity at the gateway. As noted above k, the number of measurements in a window, is determined in relationship to M, the number of spectral components above 6*qdB. Thus, the number of measurements takes out of band components above 6*qdB in to consideration, even though they may not be reconstructed at the gateway. In practice, many real world sensors have reduced sensitivity at higher frequencies and the increase in number of measurements due to out of band signals may not be prohibitive. CS sampling and reconstruction is also described in greater detail below.

Certain aspects of the present disclosure relates to methods for reducing power consumption of a pulse oximeter sensor. Commercial pulse oximeters may typically consume power in the order of 20-60 mW. The red and infrared light-emitting diodes (LEDs) account for most of this power. A power-efficient design for a PPG sensor may bring the power consumption down to 1.5 mW. The duty cycle associated with LED lighting may be reduced for a given uniform sampling rate. Fast detectors and higher clock frequencies may be used among other optimizations. Thus, the LED may be switched on for $T \cdot f_s$ duration, where $f_s$ and T represent the sampling rate and duration of lighting used to acquire each sample, respectively.

The PPG signals may be sparse in a spectral domain, and hence compressible. This may enable the usage of a compressed sensing (CS) framework in order to acquire the PPG signals. The PPG signals may be sampled at non-uniform (i.e., random) time intervals, but with an average sampling rate of $F_s$. In the CS approach, the sampling rate $F_s$ may be much smaller than the uniform sampling rate $f_s$. A factor $f_s/F_s$ may be referred as an under-sampling ratio (USR). It can be noted that this sampling approach may result in a reduced power consumption (i.e., approximately by a factor of USR) of pulse oximeter sensors used for PPG acquisition, as the LED may be lit up for only $T \cdot f_s/USR$ duration instead of $T \cdot f_s$.

A benefit of the CS-based approach compared to low pass filtering and sampling at $f_s/USR$ is that the signal content above $f_s/USR$ may not be lost. Similarly, narrow-band signals at higher frequencies may also be acquired with a high USR. Another benefit of utilizing the CS framework is that the measurements may be independent of the transform space used at reconstruction, including the Fourier space as in traditional Nyquist rate sampling.

Figure 10:
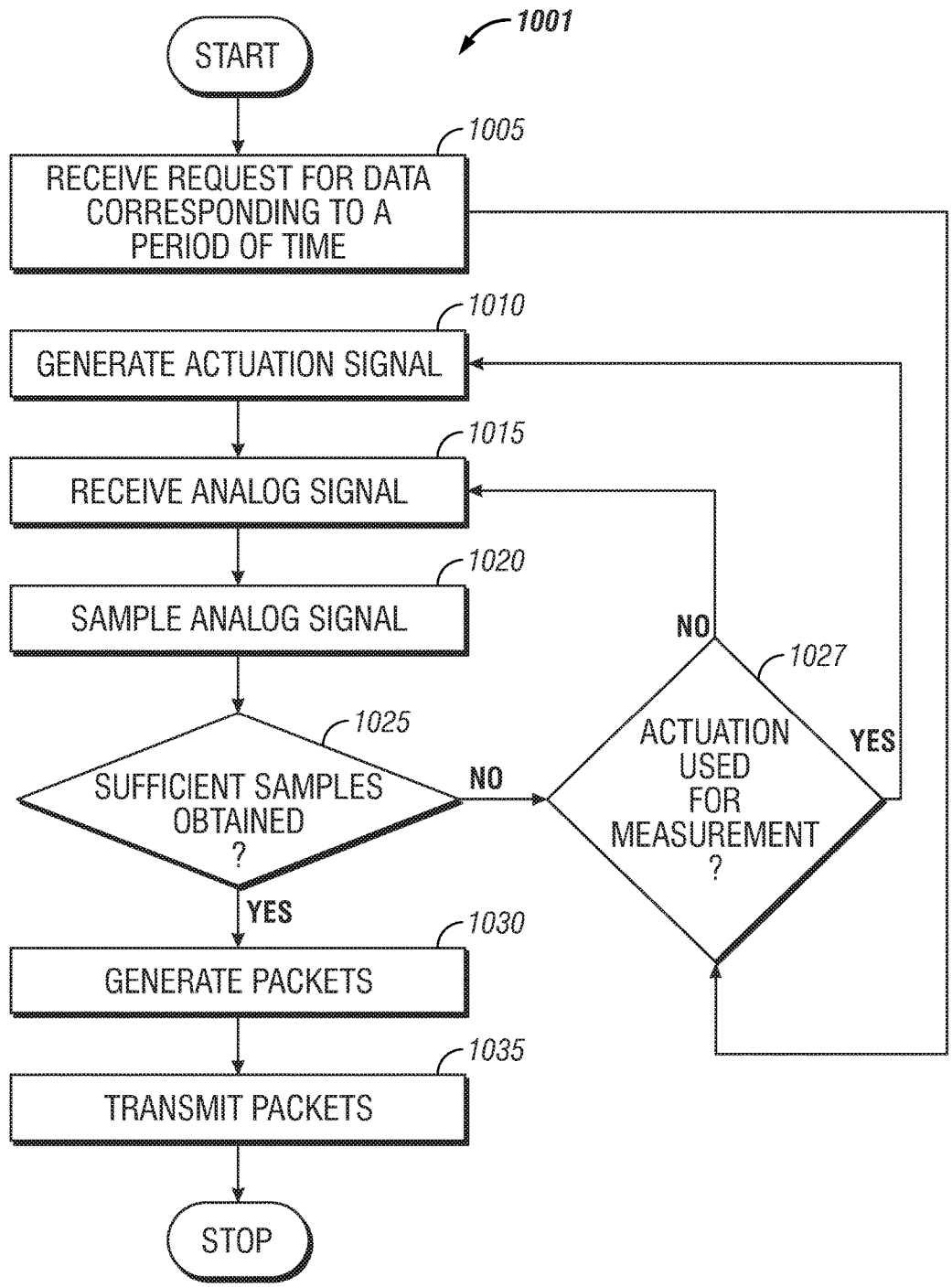
FIG. 10 is a flowchart illustrating a method of sensing data.

FIG. 10 illustrates a method 1001 of sensing data in accordance with certain aspects of the present disclosure. In one aspect, the method 1001 may be implemented in a sensor such as sensor 501 of FIG. 5. In step 1005, the sensor 501 receives a request for data corresponding to a period of time. This request may come from the gateway 610. Alternatively, the sensor 501 may be configured to periodically generate data in response to other stimuli. Continuing at step 1027, the sensor 501 determines whether or not an actuation signal is used in the particular measurement being performed. For, example, if the sensor 501 is detecting light that is generated by an LED, such as the LED 509, an actuation signal may be used to drive the LED. In this case, the method proceeds to step 1010 to generate an actuation signal and acquire additional samples. If no actuation signal is used for the particular measurement, the method proceeds to step 1015 to acquire additional samples. Continuing to step 1010, after receiving the request, the sensor 501 may generate an actuation signal. As described above, certain sensors may comprise LEDs or other circuits which are actuated in order to generate a signal that is measured by the sensor 501. As described above, other sensors, such as accelerometers may not require actuation signals and may omit this step. Continuing to step 1015, the sensor 501 receives an analog signal. The analog signal may be indicative of some vital sign or other characteristic of a person. Continuing to step 1020, the sensor 501 may sample the analog signal. In one aspect, compressed sensing is used to generate the samples.

Continuing to decision step 1025, the sensor 501 determines if a sufficient number of samples have been obtained so that the sampled signal may be accurately reproduced by the gateway 610. As described above, some number k, of samples is determined to be sufficient to accurately reconstruct the sampled signal. However, because of clock misalignment, packet losses, or other issues, additional samples may be included or a number of samples may be omitted. This number of additional or absent samples may be referred to as δ. As described herein, the gateway is able to handle reconstruction of the sampled signal when receiving k+δ samples. If the number of samples is determined to be insufficient, the method returns to decision step 1027. However, if the number of samples is sufficient, the method proceeds to step 1030. At step 1030, the sensor 1030 generates one or more packets containing the samples of the analog signal. Continuing at step 1035, the packets are transmitted to the gateway 610. Advantageously, the reduced number of samples acquired at the sensor and the reduced process performed on the sampled signal results in reduced power consumption and circuit complexity at the sensor.

Figure 11:
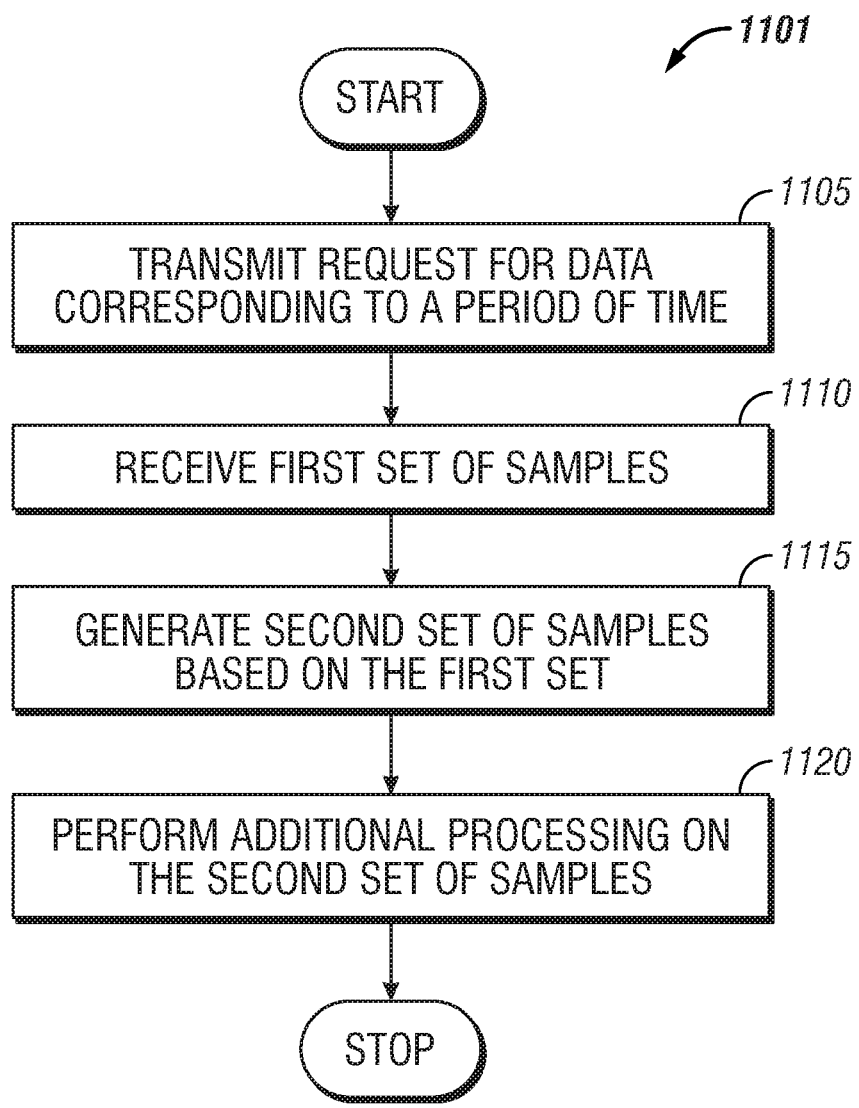
FIG. 11 is a flowchart illustrating a method of processing data.

FIG. 11 illustrates a method 1101 of processing data in accordance with certain aspects of the present disclosure. In one aspect, the method 1101 may be implemented on a gateway such as gateway 610 of FIG. 6. At step 1105, the gateway 610 transmits a request to a sensor, such as sensors 501, 550, for data corresponding to a period of time. In one aspect, step 1105 may be performed periodically or in response to a particular stimulus such as an asynchronous request or a user interaction. In another aspect, the sensor 501 may be configured to periodically or aperiodically transmit data to the gateway 610 without receiving a request. Proceeding to step 1110, the gateway receives a first set of samples from the sensor 501. As described above, the first set of samples may comprise a set of k+δ CS samples taken by the sensor 501. Proceeding to step 1115, the gateway 610 generates a second set of samples based on the first set of samples from the sensor 501. In one aspect, the second set of samples corresponds to a complete set of Nyquist samples over the period of time. The process of generating the complete set of Nyquist samples from the CS samples is described in greater detail below with respect to FIGS. 13-18. Proceeding to step 1120, the gateway 610 performs additional processing on the second set of samples. For example, the gateway 610 may mitigate packet loss, remove artifacts in the received sample set, determine and mitigate clock misalignment between the gateway 610 and the sensor 501, and analyze the second set of samples to interpret vital signs and trigger alarms. In another aspect the gateway may be configured to receive a set of samples from more than one sensor, each set corresponding to a common time period. In some aspects, each set of samples may be aligned by the gateway 610 to facilitate comparison of the sensor inputs during the common time period. Advantageously, by performing CS reconstruction at the gateway 610, the circuitry and power consumption at the sensor 510 may be significantly reduced.

Figure 12A:
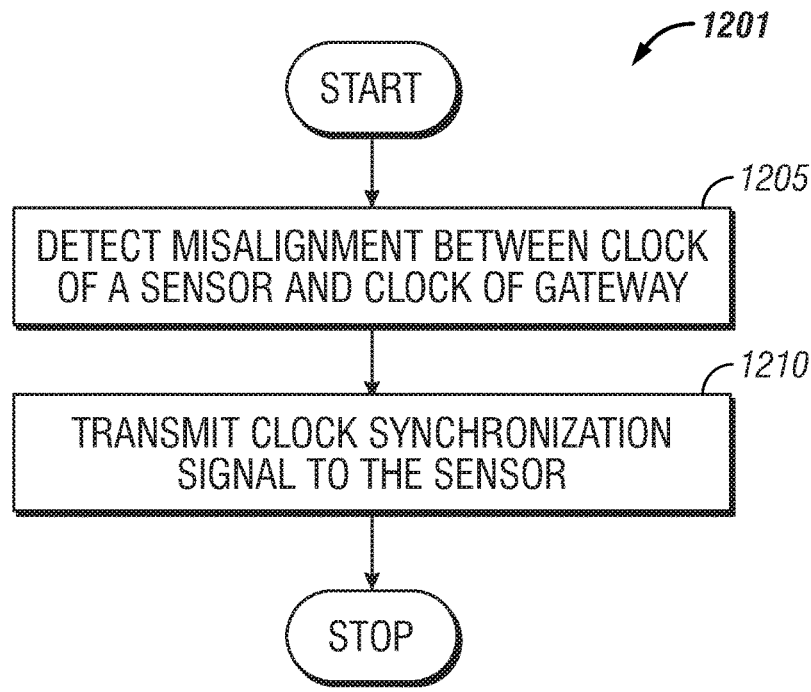
FIG. 12A is a flowchart illustrating a method for handling clock misalignment.

FIG. 12A illustrates a method 1201 for handling clock misalignment in accordance with certain aspects of the present disclosure. In one aspect, the method 1201 may be implemented on a gateway such as gateway 610 of FIG. 6. In some communication systems, when there is a clock mismatch between sender and receiver, sample insertion/deletion at one of the nodes may be performed to keep real time buffers from running empty or overflowing. If proper care is not taken with sample insertion and deletion, discontinuities resulting from this operation may lead to undesirable artifacts. The complexity and the cost of a device depend on the accuracy of the desired clock. For instance, a device synchronized to the GPS clock will be more expensive than a device operating with a clock based on a ±20 parts per million (ppm) crystal. Similarly, a device operating with a clock based on a ±75 ppm crystal will be further economical. In the gateway 610 with CS reconstruction, Nyquist samples are reconstructed at the gateway based on measurements at the sensor. In some aspects, the gateway 610 typically has better clock management and closer to the real wall-clock (such as GPS). This will enable the gateway 610 to synchronize streams of data from multiple sensors, even when the number of measurements is k±δ, where δ comprises the number of measurements due to clock mismatch. In some embodiments, the δ value may be different for one or more of the multiple sensors. In addition, the δ value may change over time for each sensor. Regardless, as described herein, the receiver with CS reconstruction is capable of coping with varying number of measurements for a given window of observation. The receiver may accomplish this by reconstructing N Nyquist samples for each of the sensors 501, 550, where N corresponds to the window of observation based on the clock at the gateway.

Figure 19C:
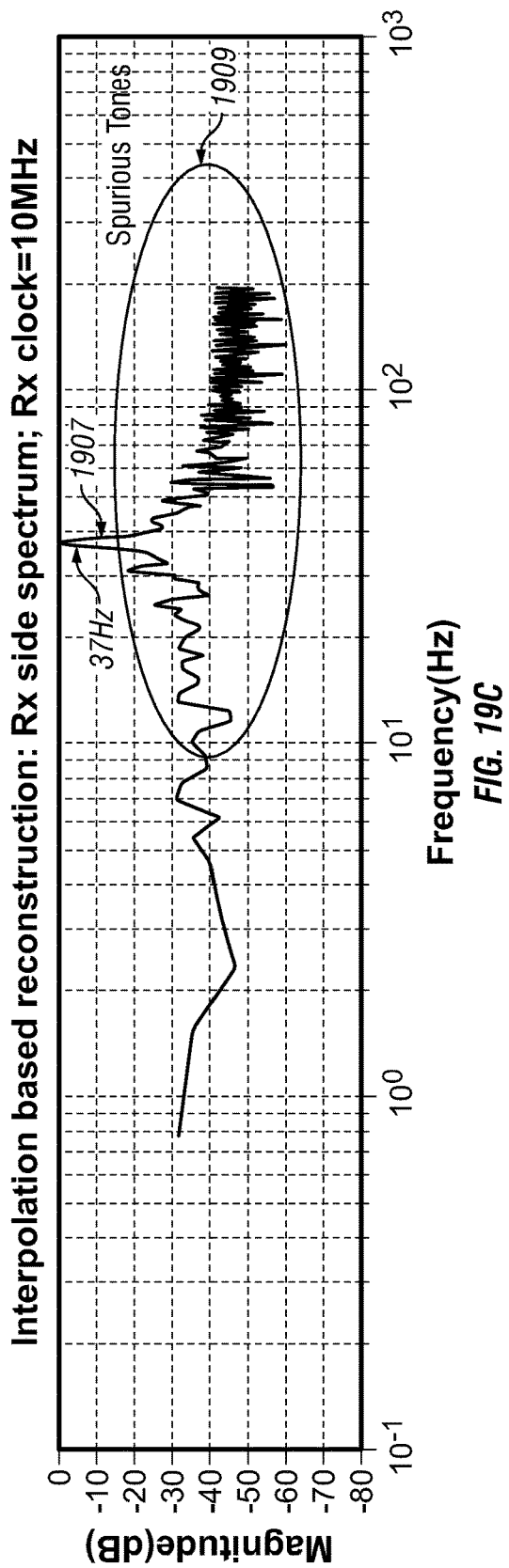

This clock mismatch coping ability of CS reconstruction and its advantages are described further with respect to FIGS. 19A-C and 20A-C. FIG. 19A illustrates a waveform 1903 as detected at a sensor/transmitter. As shown in the figure, the clock rate of the transmitter is 10.1523 MHz. As illustrated a significant component of the waveform 1903 is present at 37 Hz. FIG. 19B illustrates a reconstruction 1905 of the waveform 1903 generated at the receiver/gateway. As shown, the clock rate at the receiver is 10 MHz. Accordingly, there is a mismatch of clock rates between the transmitter and receiver. As illustrated, in FIG. 19B, the clock mismatch between the transmitter and the receiver has minimal effect on the reconstruction using CS techniques. Thus, the reconstructed waveform 1905 is substantially similar to the waveform 1903 of FIG. 19A despite the clock mismatch. As described above, the samples used in CS reconstruction may not be regularly spaced over the period of the sampled signal. This non-uniform sampling facilitates, in part, the accurate reconstruction despite clock mismatch. FIG. 19C illustrates another reconstruction 1907 of the waveform 1903 of FIG. 19A. As with the waveform 1905 of FIG. 19B, the clock rate of the receiver/gateway is 10 MHz. Thus, the same clock mismatch is present. However, the reconstruction 1907 is generated using traditional interpolation based reconstruction. As shown, interpolation based reconstruction under the conditions of clock mismatch results in spurious tones 1909 in the reconstruction 1907. In part, the spurious tones may result from traditional clock mismatch mitigation. For example, one technique involves deleting two samples and inserting a sample linearly interpolated with its neighbors to maintain the receiver buffer from over flowing because of the mismatch. Advantageously, using CS techniques, such mitigation schemes are unnecessary. Thus, accurate reconstruction can occur despite clock mismatch conditions. As noted above, this also enables simpler, less power intensive clock circuitry to be used at the sensor without negatively affecting the data received at the gateway.

Figure 20A:
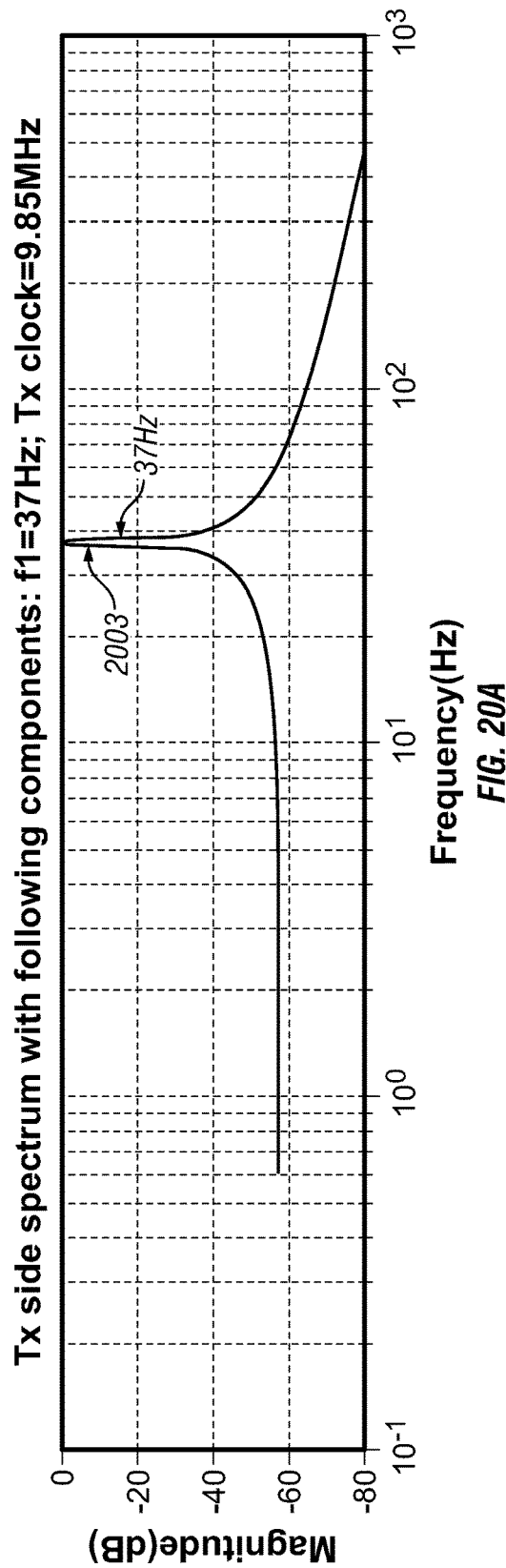
FIG. 20A-C illustrate additional waveforms depicting the effect of a clock mismatch between a transmitter and receiver with transmitter clock rate lower than receiver clock rate in accordance with certain aspects of the present disclosure.
Figure 20B:
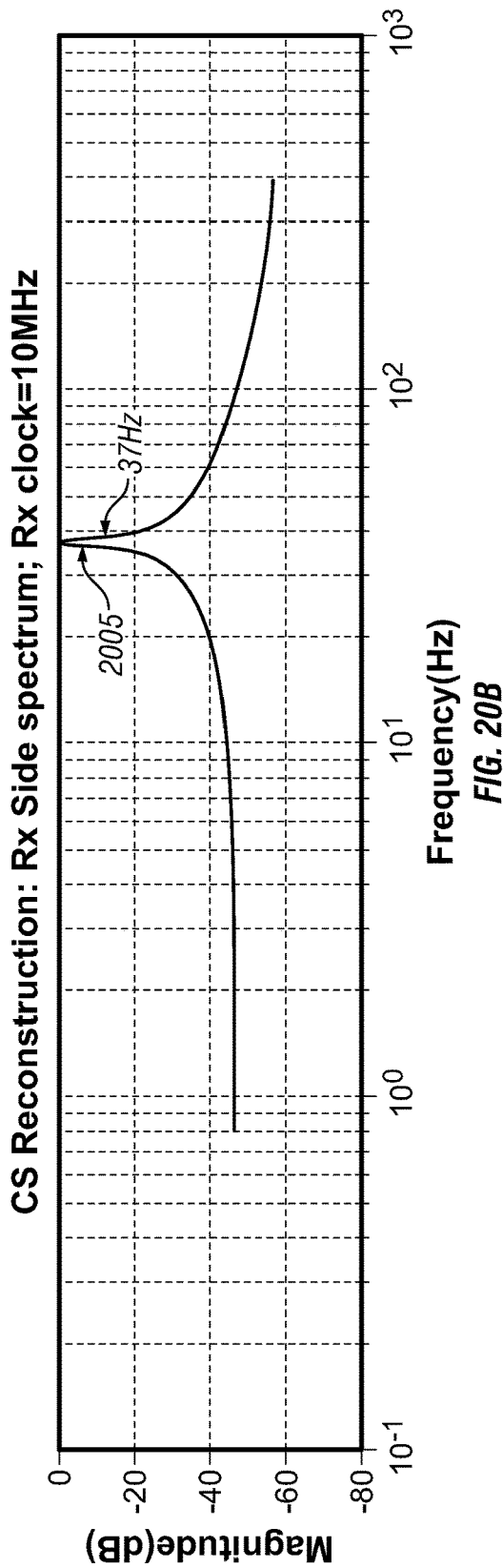
Figure 20C:
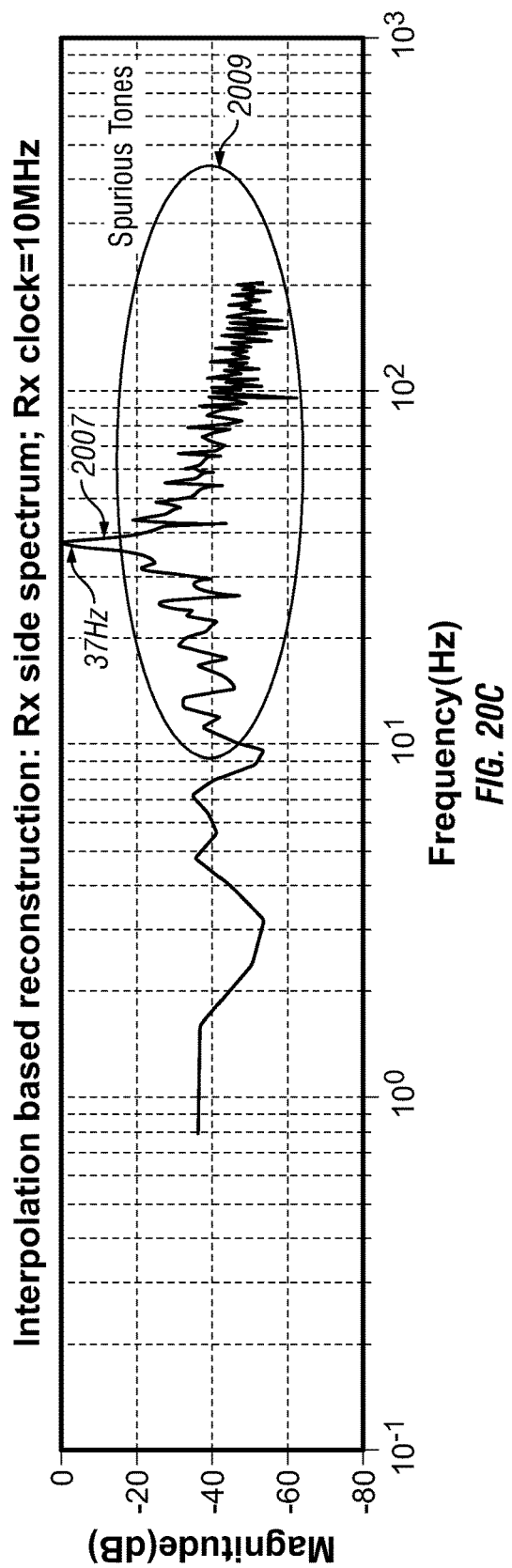

FIGS. 20A-C are similar to FIGS. 19A-C, but illustrate reconstructions where the transmitter/sensor has a clock rate that is misaligned from and slower than the clock rate of the receiver/gateway. FIG. 20A illustrates a waveform 2003 as detected at a sensor/transmitter. As shown in the figure, the clock rate of the transmitter is 9.85 MHz. As illustrated a significant component of the waveform 2003 is present at 37 Hz. FIG. 20B illustrates a reconstruction 2005 of the waveform 2003 generated at the receiver/gateway. As shown, the clock rate at the receiver is 10 MHz. Accordingly, there is a mismatch of clock rates between the transmitter and receiver. As illustrated, in FIG. 20B, the clock mismatch between the transmitter and the receiver has minimal effect on the reconstruction using CS techniques. Thus, the reconstructed waveform 2005 is substantially similar to the waveform 2003 of FIG. 20A despite the clock mismatch. As described above, the samples used in CS reconstruction may not be regularly spaced over the period of the sampled signal. This non-uniform sampling facilitates, in part, the accurate reconstruction despite clock mismatch. FIG. 20C illustrates another reconstruction 2007 of the waveform 2003 of FIG. 20A. As with the waveform 2005 of FIG. 20B, the clock rate of the receiver/gateway is 10 MHz. Thus, the same clock mismatch is present. However, the reconstruction 2007 is generated using traditional interpolation based reconstruction. As shown, interpolation based reconstruction under the conditions of clock mismatch results in spurious tones 2009 in the reconstruction 2007. In part, the spurious tones may result from traditional clock mismatch mitigation. For example, one technique involves inserting a sample linearly interpolated with its neighbors to maintain the receiver buffer from under flowing because of the mismatch. Advantageously, using CS techniques, such mitigation schemes are unnecessary. Thus, accurate reconstruction can occur despite clock mismatch conditions. As noted above, this also enables simpler, less power intensive clock circuitry to be used at the sensor without negatively affecting the data received at the gateway.

As noted above, the gateway 610 may have superior clock management compared with clock management on low power sensors 501 and 550. The gateway 610 can send messages to the sensors, 501 and 550 that may be periodic or aperiodic, causing them to synchronize them to the clock at gateway 610. This is illustrated in method 1201. In step 1205, the gateway 610 detects a misalignment between the clock of the gateway 610 and the clock of the sensor 501. Proceeding to step 1210, gateway 610 may transmit a clock synchronization signal to the sensor 501. In some aspects, step 1210 may be performed responsive to the determination in step 1205. In other aspects, step 1201 may be performed periodically or in response to other stimuli. In another aspect, gateway 610 may be in communication with a plurality of sensors 501 and 550. Gateway 610 may broadcast a clock synchronization signal to some or all of the plurality of sensors 501 and 550.

Advantageously, the aspects described with respect to FIGS. 11 and 12A may be combined. Thus, for example, the gateway 610 may maintain its own first clock according to relatively precise circuitry. Similarly, the sensor 501 may maintain its own second clock according to relatively imprecise circuitry. As described above, the sensor 501 generates a set of samples, such as CS samples, according to its second clock signal and transmits the set to the gateway 610. Similarly, the gateway 610 may generate a second set of samples, such as a full set of Nyquist samples, according to its own first clock based on the received set of samples. Either periodically, in response to detection to misalignments between the clocks, in response to requests from the sensor 501, or in response to other stimuli, the gateway 610 may transmit a clock synchronization signal to the sensor 501.

Figure 12B:
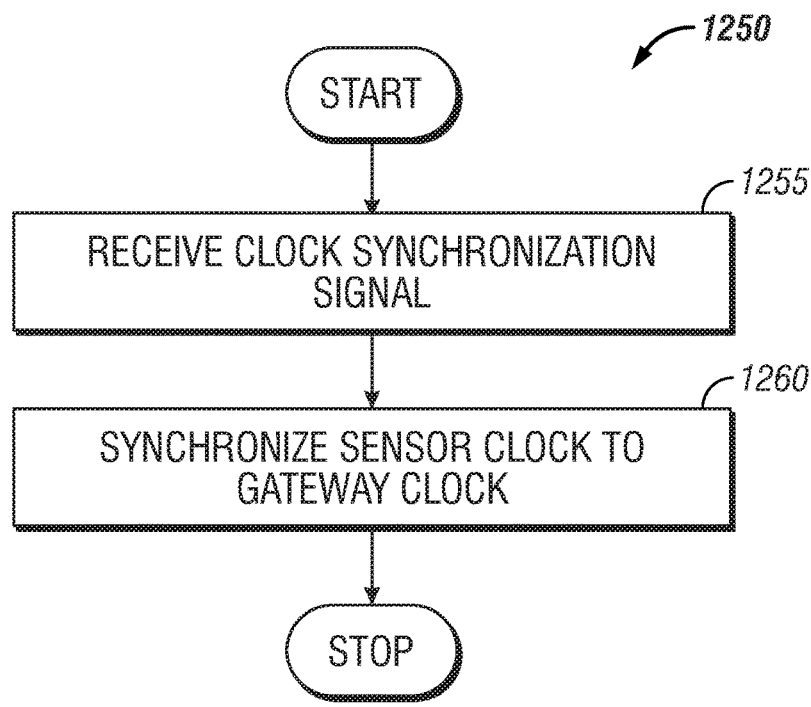
FIG. 12B is a flowchart illustrating another method for handling clock misalignment.

FIG. 12B illustrates a method 1250 for handling clock misalignment in accordance with certain aspects of the present disclosure. In one aspect, method 1250 is implemented in a sensor such as the sensor 501 in FIG. 5. In step 1255 the sensor receives a clock synchronization signal from a gateway such as the gateway 610. Proceeding to step 1260, the sensor 501 synchronizes its clock to the clock of gateway 1260.

Figure 13:
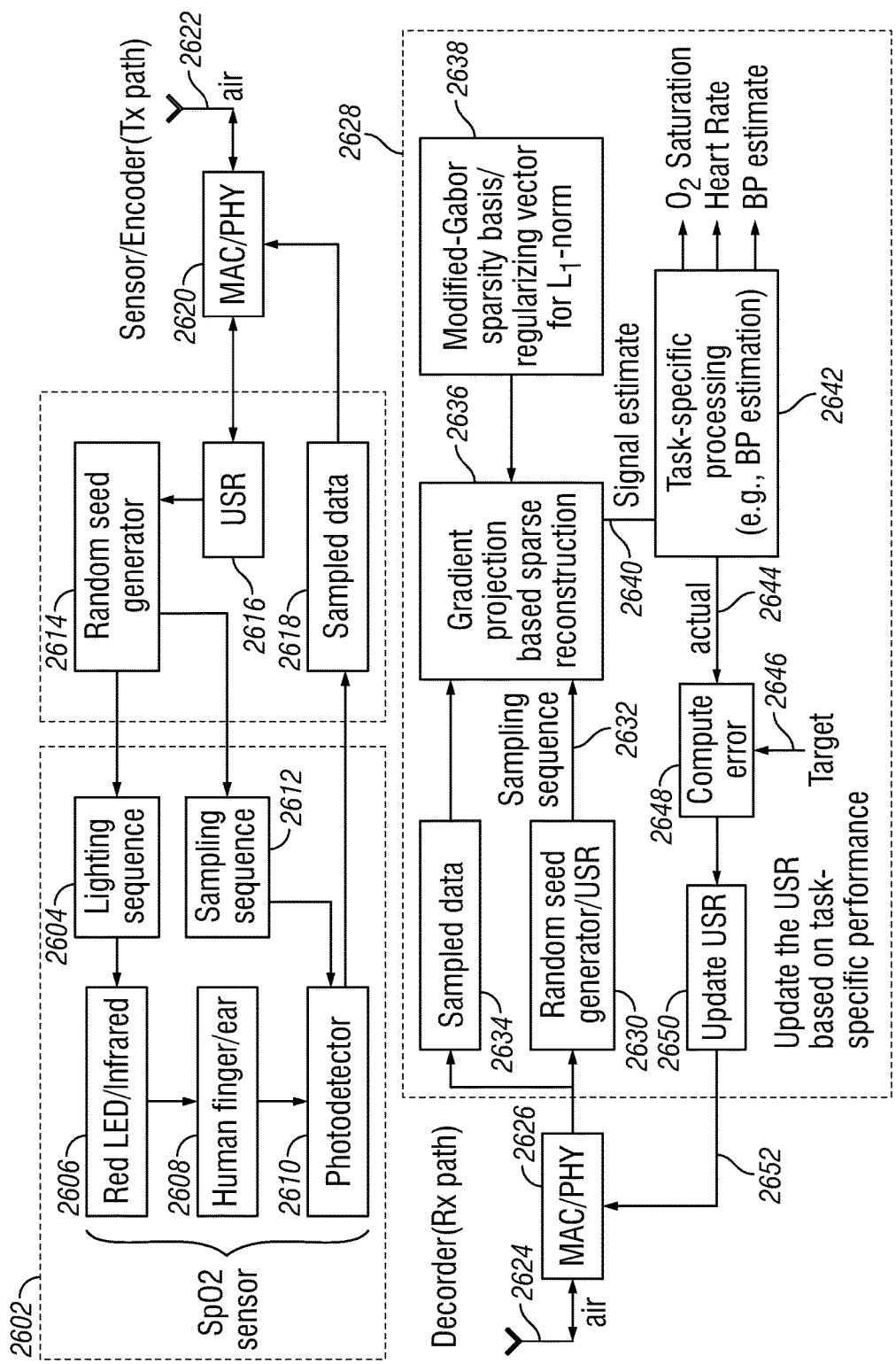
FIG. 13 illustrates an example block diagram of a sensor and a re-constructor in accordance with certain aspects of the present disclosure.

FIG. 13 illustrates an example block diagram for sensing and reconstruction of biomedical signals. A sensor 2602 for acquiring biomedical signals, such as a PPG signal, may comprise three main components: LEDs 2606, a photo-detector 2610, and lighting and sampling sequence for LED and photo-detector 2604 and 2612, respectively. The LEDs 2606 may emit light with wavelengths between 600 nm and 1000 nm, which also comprises red and infrared parts of the spectrum. The light from the LEDs 2606 may be transmitted/reflected from a tissue 2608 (e.g., a human finger or ear, as illustrated in FIG. 13) and may be collected on the photo-detector 2610. The ratio of the average intensities corresponding to the LEDs measured at the photo-detector may be useful in determining the oxygen content ($S_pO_2$) in blood. Thus, $S_pO_2$ may be a function of the mean (DC content) of the PPG signal.

The lighting sequence 2604 and the sampling sequence 2612 may be obtained using a random seed generated by a seed generator 2614 according to a defined under-sampling ratio (USR) 2616. The sampled data 2618 from the photo-detector 2610 may be sent for Media Access Control/Physical Layer (MAC/PHY) processing 2620 before transmission. The processed samples may be then packetized and transmitted by one or more antennas 2622.

At a receiver side, as illustrated in FIG. 13, the transmitted samples may be received at one or more antennas 2624 and processed by MAC/PHY block 2626. The data may be then passed to a re-constructor 2628 for obtaining the biomedical signal at Nyquist rate. For the accurate reconstruction, a random seed generator 2630 that generates a sampling sequence 2632 may need to be synchronized with the random seed generator 2614 of the sensor.

In one aspect of the present disclosure, a gradient based sparse reconstruction 2636 may be applied on sampled data 2634 by using, for example, a modified-Gabor sparsity basis regularizing vector for $l_1$-norm 2638. An estimated signal 2640 may be then utilized by unit 2642 for task-specific processing in order to obtain, for example, a blood pressure estimate, a level of the oxygen in blood, and a heart rate. The reconstructed data from other sensors such as 550 comprising ECG data or 3D-accelerometer data may be available to 2642 for such task specific processing. An actual signal 2644 may be compared with a target signal 2646 by unit 2648 in order to update USR utilized for generating sampling instances. An updated USR value 2652 at the output of unit 2650 may be used by the random seed generator 2630, and may be also fed back to the sensor for adapting the USR 2616 of the sensor. Beside the USR, additional feedback information may be also transmitted to the sensor for adapting some other parameters, such as: a number of measurements at the sensor, coefficients of a measurement matrix, a number of transmitted samples of the signal, and a number of samples in each transmitted packet.

Modulations in the PPG waveform (associated with either red or infrared LEDs) may be related to the instantaneous blood flow. Instantaneous heart rate (HR) may be estimated as the inverse of the distance between waveform peaks. The lighting sequence for the LEDs may depend upon the desired sampling rate for the PPG signal. It may be assumed a uniform Nyquist sampling rate. Also, it can be noted that frequent lighting of the LEDs may result in significant power consumption of the pulse oximeter sensor.

Certain aspects of the present disclosure support exploiting the sparse nature of the PPG signal and making fewer measurements in order to save the sensor power. A Gabor basis may be employed as the transform space consisting of various cosine waves with time support limited by Gaussian window functions at different scales.

Let the original sampled PPG signal be denoted by N-dimensional vector x and the sparse-domain transform basis be represented by N×N matrix W. The (i, j) entry of matrix W may be given as:

$$[W]_{i,j} = \cos\left(\frac{2\pi(i-1)(j-1)}{2N}\right) \times \exp\left(-\frac{(i-1)^2(j-N/2)^2}{wN^2}\right). \quad (1)$$

The term w from equation (1) may be associated with the width of the Gaussian kernel in the Gabor basis. Each row of the matrix W may be normalized such that the corresponding $l_2$-norm is equal to 1, and the matrix W may be referred as the sparse-basis. The PPG signal x may be projected on the sparse-basis to generate the corresponding N-dimensional representation in the Gabor transform space and it may be given as:

$$y = W \cdot x. \quad (2)$$

Figure 14A:
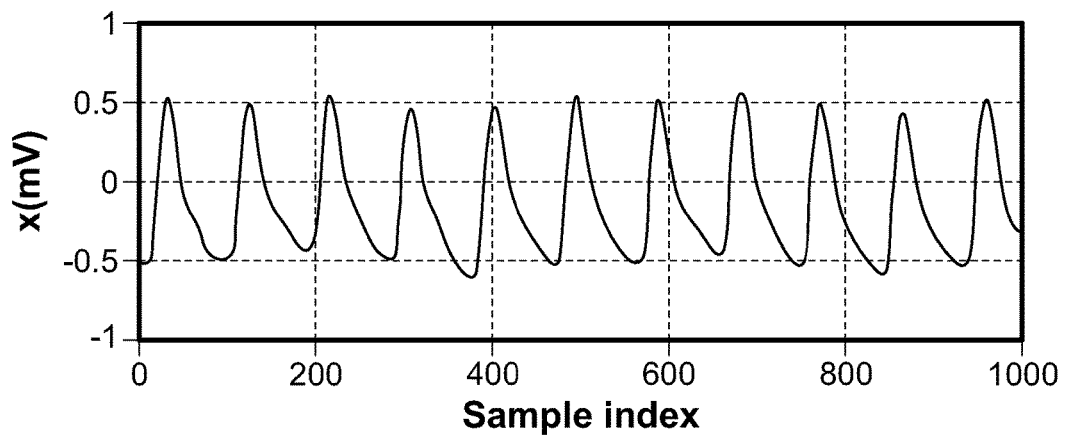
FIG. 14A-B illustrates an example of a PPG signal and its transform in the Gabor space in accordance with certain aspects of the present disclosure.
Figure 14B:
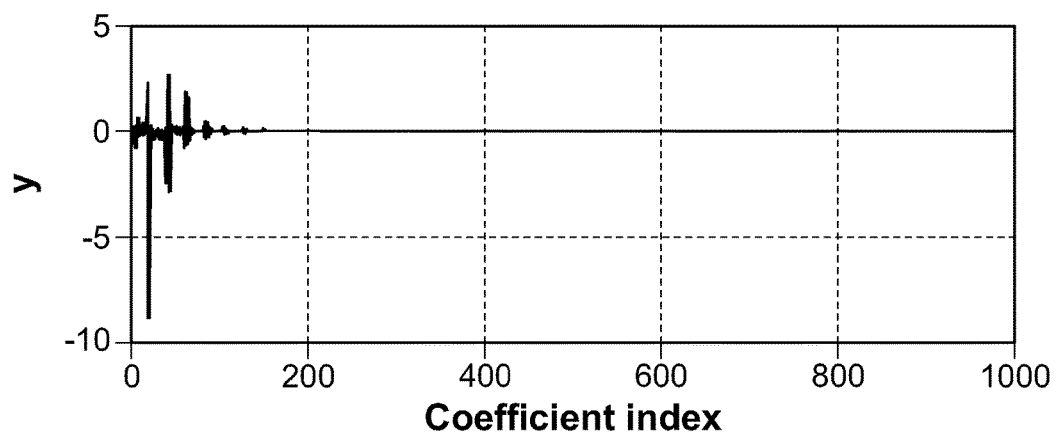

FIG. 14A illustrates an example of a short segment of a PPG signal and a corresponding representation y in the Gabor transform space in accordance with certain aspects of the present disclosure. FIG. 14B illustrates the eight-second segment sampled at 125 Hz (i.e., a total of N=1000 samples). It can be observed that the signal x may be sparse and compressible in the transform domain with about 30 coefficients greater than 0.2 in terms of absolute magnitude. This indicates that most of the PPG signal characteristics may reside in a much lower-dimensional space compared to N and thus the PPG signal may be compressible.

Therefore, the CS principles may be exploited which allows to make K<<N measurements (i.e. to heavily undersample the original data) and still be able to estimate x with a high fidelity. If the signal x is explicitly-sparse with only M non-zero elements in the transform space, then selecting K≥M log N/M samples at random from x may provide sufficient information with a high probability to enable signal reconstruction with zero error.

In real situations, the signal may never be truly sparse and some information content may exist throughout the transform-space. However, the number of significant components with magnitude greater than ε, where ε<<max(y), may be much smaller than N. In FIG. 14, value of ε is 0.2. This approach may be extended to the case where x is not explicitly-sparse, and the CS paradigm may still remain valid. However, the reconstruction error may not be exactly equal to zero.

The sensing process for x may be mathematically expressed. Let P denote a K-dimensional vector containing unique entries (for example, chosen at random) with each element bounded between 1 and N. This may essentially provide K random locations to select the elements from x. The seed for random number generation for constructing the vector P may be generated locally at the sensor or at the receiver. The seed may be based on keys used in security protocols of the communication link. The K-dimensional measurement vector r, obtained from x, may be written as:

$$r = H \cdot x, \quad (3)$$

where H denotes the K×N measurement matrix.

The $i^{th}$ row of the matrix H from equation (3) may be an all-zero vector with 1 at the location given by the $i^{th}$ element of P. It can be noted that in the CS framework the measurement matrix may be defined as a matrix containing random independent and identically distributed (i.i.d.) elements. Such a measurement matrix may be necessary when it is not known a priori that the input signal is sparse in the time domain or in the transform domain. In practice, the sensing process may be implemented as $\Delta_i$=MINDUR*USR+J(i), where $\Delta_i$ is the duration between $(i-1)^{th}$ and $i^{th}$ sampling instances, MINDUR is the minimum duration with uniform Nyquist sampling, USR is the under sampling ratio, and J(i) is some random jitter introduced for the $i^{th}$ sample such that J(i)≤MINDUR.

The matching pursuit (MP) algorithm may be employed for signal reconstruction from the measurement vector r. The MP technique represents a greedy algorithm that builds up a signal approximation iteratively by making a locally optimal decision. An initialization of the MP algorithm may be given by defining a modified basis V=H·W of dimension K×N such that V=[$V_1$ ... $V_N$], where $V_j$ is the $j^{th}$ column vector of V. Then, the residual may be initialized as $r_0$=r, with an approximation that $\hat{y}$=0. The dimensionality of vector $\hat{y}$ is the same as the dimensionality of y (i.e., N). The iteration counter may be also initialized as i=1.

After that, the column vector from V may be found that maximizes the inner-product of the residual $r_{i-1}$ onto V:

$$n_i = \arg\max_{j=1...N} \frac{\langle r_{i-1}, V_j \rangle}{\|V_j\|_{L_2}}. \quad (4)$$

Then, the residual may be updated, and the coefficient vector y may be estimated as follows:

$$r_i = r_{i-1} - \frac{\langle r_{i-1}, V_{n_i} \rangle}{\|V_{n_i}\|_{L_2}^2} V_{n_i}, \quad (5)$$

$$\hat{y}_{n_i} = \hat{y}_{n_i} + \frac{\langle r_{i-1}, V_{n_i}\rangle}{\|V_{n_i}\|_{l_2}^2}. \quad (6)$$

After that, the iteration counter i may be incremented, and $$\Delta_i = \frac{\|r_i\|_{l_2}}{\|r\|_{l_2}}$$

may be defined. If i<m and $\Delta_i$>ε, then the algorithm step defined by equation (4) may be repeated. Otherwise, $\hat{\Delta}=\Delta_i$ and î=i and the algorithm may proceed to the step defined by equations (5) and (6). Finally, the original estimates may be obtained as $\hat{x}=W\cdot\hat{y}$.

The term m represents the upper-bound on the number of iterations allowed for reconstruction, and the term ε defines the convergence criterion. Intuition behind the MP algorithm is twofold. At each iteration step, the algorithm may attempt to find the column of V that may be most strongly correlated with the residual of r, and then may subtract the contribution of this column vector from r. This algorithm is greedy in nature because at each step it may estimate the most dominant component of the original signal x in the projection space W. It can be also noted that the main complexity of the MP algorithm lies in equation (4) which may cost O(K·N) arithmetic operations for a single iteration.

Certain aspects of the present disclosure use the gradient-projection based sparse reconstruction (GPSR) approach to obtain a reconstructed signal from the measurement vector r. This approach may estimate the original signal x by jointly minimizing a data fidelity term (i.e. $l_2$ norm of the error) and the $l_1$-norm in a transform space (i.e. measure of sparsity) under no constraints. It is proposed in the present disclosure to modify this optimization problem by using a weighted $l_1$-norm. The reconstruction algorithm may be given as:

$$\min_x \|Hx-r\|^2 + \tau \sum_{i=1}^{N} |[f]_i[W\cdot x]_i|, \quad (7)$$

where f is a N-dimensional vector providing the relative importance of coefficients in transform space for computing the measure of sparsity (i.e., $l_1$-norm). The quantity 2 is a non-negative parameter indicating the relative weight of $l_2$-norm and $l_1$-norm in the cost function. The terms $[f]_i$ and $[W\cdot x]_i$ denote the $i^{th}$ element of vectors f and $[W\cdot x]_i$, respectively.

The $i^{th}$ element of vector f may be given by:

$$[f]_i = \frac{1}{[W\cdot \bar{x}]_i + \sigma}, \quad (8)$$

where σ is a small regularizing parameter. The quantity $\bar{x}$ represents the ensemble mean of the original signal vector x, and may be estimated by averaging training example vectors. A segment from the MIMIC database may be utilized to estimate $\bar{x}$, which can be then excluded from the experimental validations described below.

Figure 15:
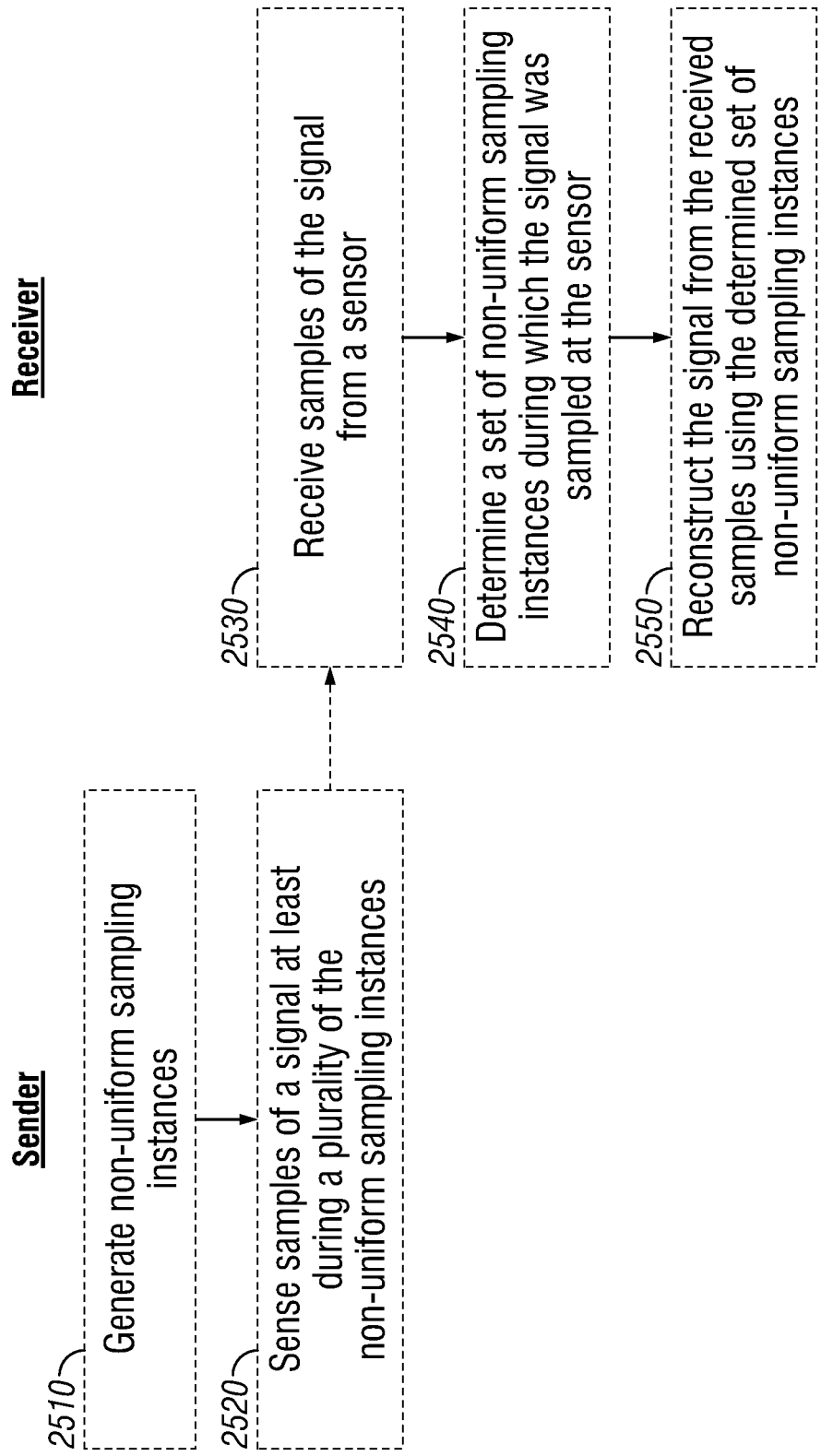
FIG. 15 illustrates example operations for under-sampled acquisition and reconstruction in accordance with certain aspects of the present disclosure.

FIG. 15 illustrates example operations for under-sampled acquisition at a sensor and reconstruction at a receiver in accordance with certain aspects of the present disclosure.

Figure 16:
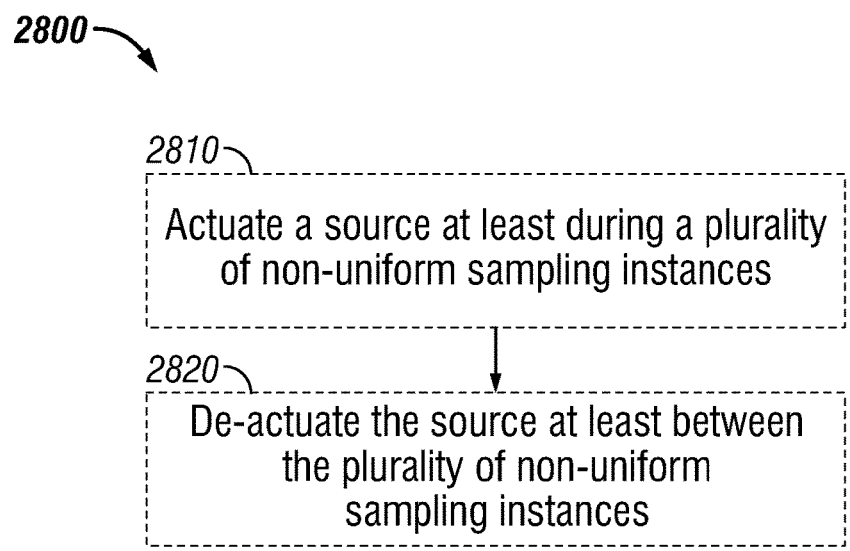
FIG. 16 illustrates example operations for actuating and de-actuating a source at the sensor in accordance with certain aspects of the present disclosure.

FIG. 16 illustrates example operations 2800 for actuating and de-actuating a light source at the sensor. As described below, the operations illustrated in FIGS. 15 and 16 may be related. Thus, for the purposes of explanation, FIGS. 15 and 16 are described jointly herein. At step 2510 of FIG. 15, non-uniform sampling instances may be generated at the sensor according to a random seed. At step 2520, samples of a signal may be sensed at least during a plurality of the non-uniform sampling instances. At step 2810 of FIG. 16, the source at the sensor may be actuated, for example, by turning on one or more LEDs at least during the plurality of the generated non-uniform sampling instances, and the sensor may be de-actuated, at step 2820, at least between the plurality of the non-uniform sampling instances.

The sensed samples of the signal may be then packetized to obtain at least one packet of the sensed samples, and the obtained at least one packet may be transmitted over a wireless channel. At step 2530 of FIG. 15, samples of the signal may be received from the sensor at a re-constructor. At step 2540, a set of non-uniform sampling instances may be determined at the re-constructor during which signal was sampled at the sensor according to said random seed. In one aspect, the seed for non-uniform sampling sequence may be generated at the re-constructor based on keys used in security protocols of a communication link between the sensor and the re-constructor. In another aspect, the seed for non-uniform sampling sequence may be determined at the sensor and conveyed to the re-constructor (i.e., to the receiver). In yet another aspect, the seed for non-uniform sampling sequence may be determined at the receiver and conveyed to the sensor. At step 2550, the signal may be reconstructed from the received samples using the determined non-uniform sampling sequence according to, for example, the modified GPSR algorithm defined by equations (7)-(8).

The non-uniform sampling instances may be synchronized with received samples of the signal for accurate reconstruction of the signal. Information observed during the reconstruction (e.g., at least one of: coefficients related to the reconstructed signal, a number of dropped packets during the transmission, a channel signal-to-noise ratio, or the variables $\hat{\Delta}$ and î) may be utilized to adapt various sensor parameters (e.g., the USR, the number of measurements K, the number of transmitted samples of the signal N, the number of samples of the signal in each transmitted packet P, and the measurement matrix H) by conveying the observed information to the sensor via a feedback mechanism. Then, the non-uniform sampling instances may be adapted at the sensor according to the received feedback information.

Figure 17:
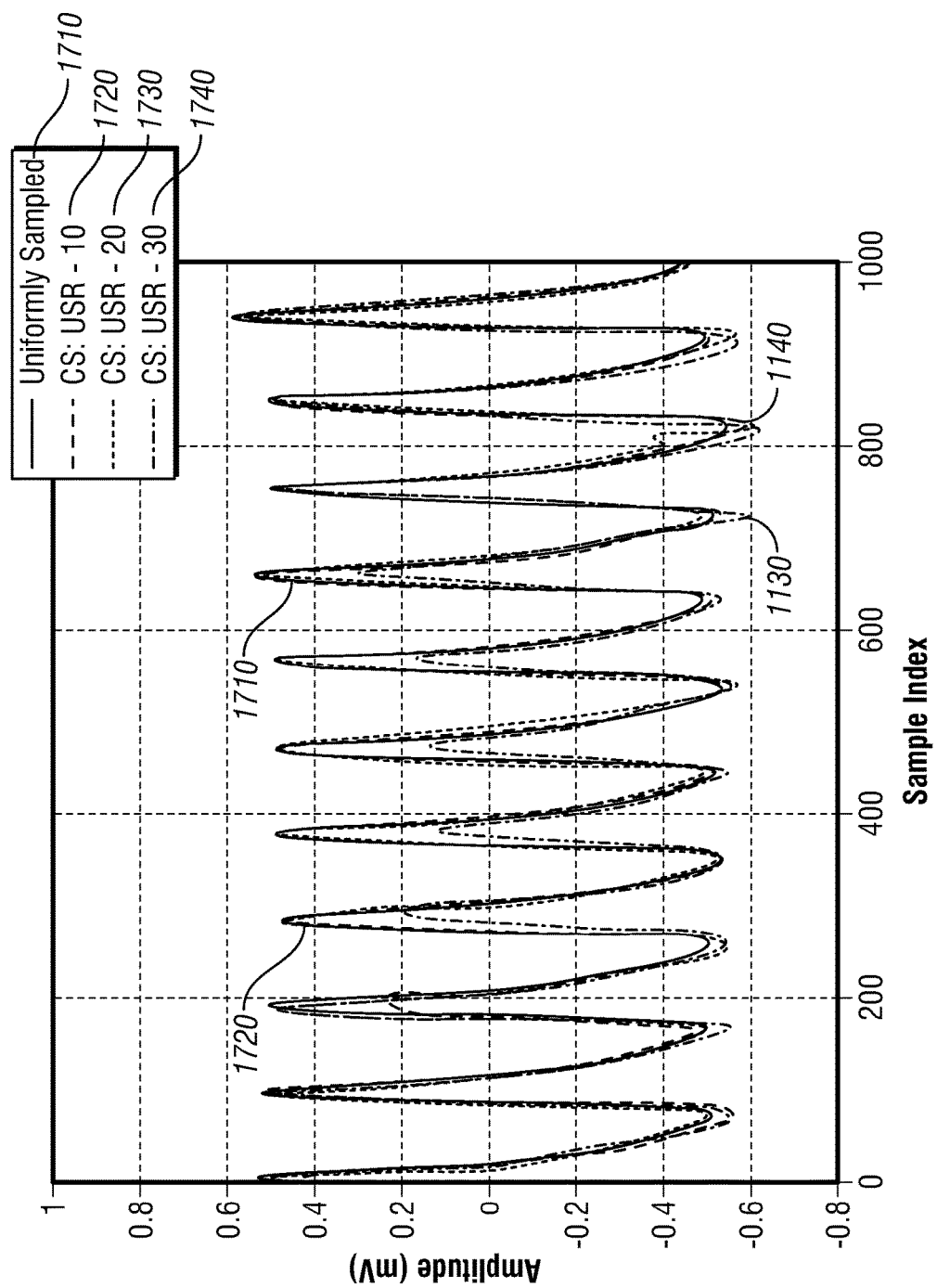
FIG. 17 illustrates a comparison of reconstructed signals obtained using different under-sampling ratios (USRs) in accordance with certain aspects of the present disclosure.
Figure 18:
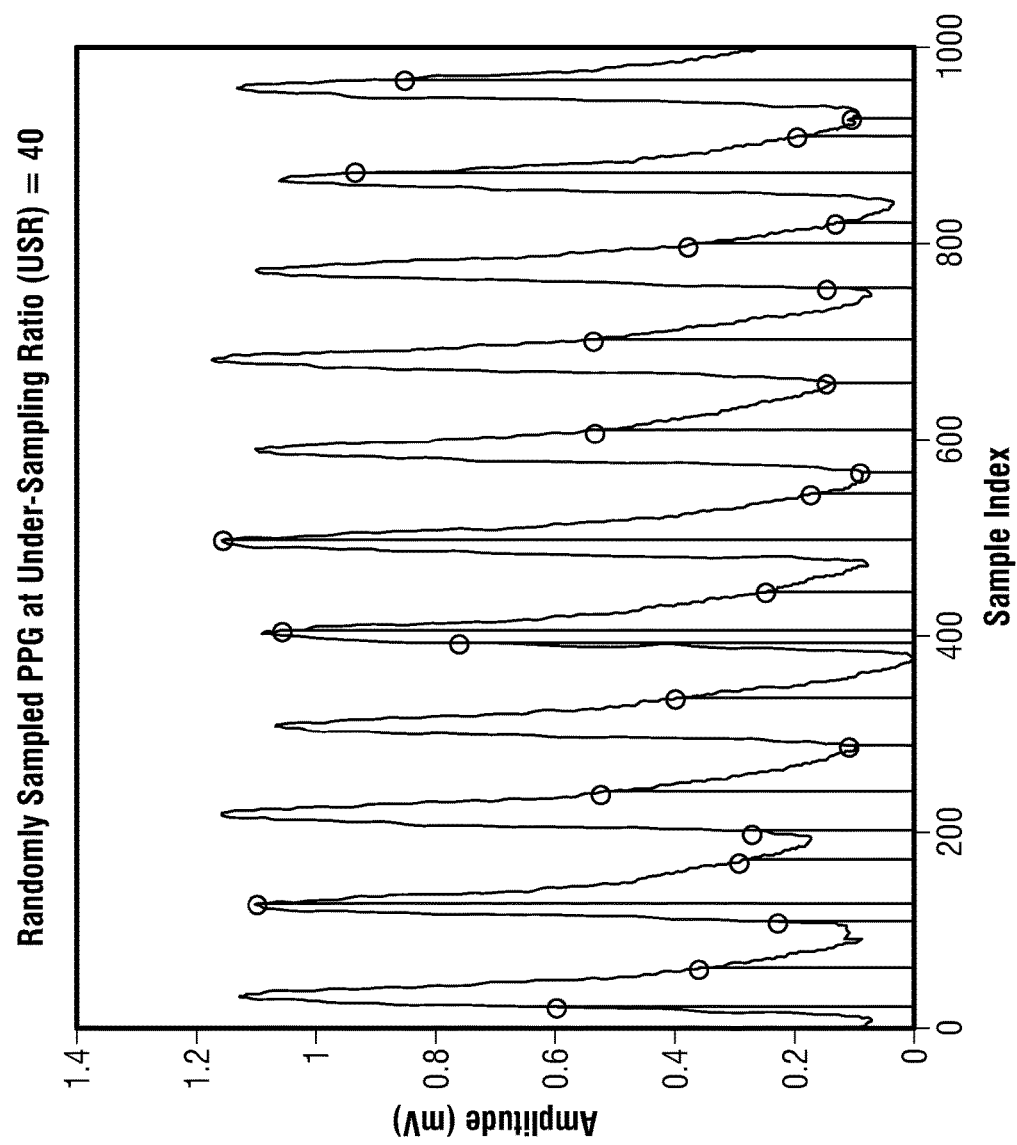
FIG. 18 illustrates an example of a signal sensed at non-uniform sampling instances in accordance with certain aspects of the present disclosure.

Some reconstruction examples generated based on the CS approach are presented in this disclosure. The eight-second segment may be selected from the MIMIC database sampled at 125 Hz (i.e., N=1000 samples). It can be recalled that the number of CS samples is K that defines an under-sampling ratio (USR) as N/K. FIG. 17 illustrates an example for the CS-PPG signal reconstructions obtained for the USR of 10, 20 and 30 with the upper bound on the number of MP iterations m equal to 500. The curve 1710 represents the uniformly sampled original signal and curves 1720, 1730 and 1740 represent reconstructed signals for values of USR of 10, 20 and 30, respectively. FIG. 18 illustrates an example of the signal sensed at non-uniform sampling instances at the USR of 40. The sampling instances are shown as vertical lines.

It can be observed from FIG. 17 that the signal integrity may be well preserved until the USR of 20, and may start degrading thereafter. However, it can be noted that the signal peak locations may be well preserved even with high USR (i.e., the USR value of 30). In this case, the LED power consumption (as a part of the PPG data acquisition) may be significantly reduced by the factor of USR because the LEDs may be lightened for much smaller duration, specifically for only $T \cdot f_s / USR$ seconds instead of $T \cdot f_s$ seconds.

Figure 22:
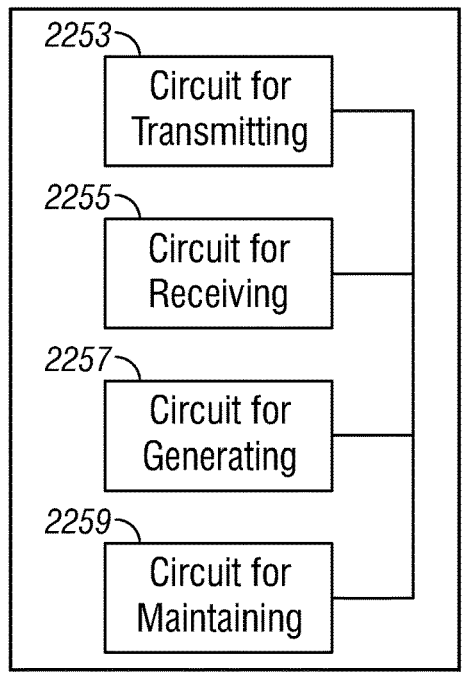
FIG. 22 is a block diagram of an apparatus in accordance with certain aspects of the present disclosure.

In some aspects, one or more of the functions recited herein are implemented in a circuit configured to perform the one ore more functions. Similarly, the means described above may comprise one or more circuits configured to implement the functionality of the means. For example, FIG. 22 illustrates aspects of a wireless communication device 2350. The wireless communication device may correspond to a gateway such as the gateway 610 of FIG. 6. In one aspect, the communication device 2250 comprises a circuit for transmitting 2253, a circuit for receiving 2255, a circuit for generating 2257, and a circuit for maintaining 2259. The circuit for transmitting 2253 may correspond to the BAN Radio 613 or the BAN Radio 613 in conjunction with the BAN MAC 616 and the processing system 619 of FIG. 6. The circuit for receiving 2255 may correspond to the BAN Radio 613 or the BAN Radio 613 in conjunction with the BAN MAC 616 and the processing system 619 of FIG. 6. The circuit for generating 2257 may correspond to the processing system 619. The circuit for maintaining 2259 may correspond to the processing system 619.

Figure 23:
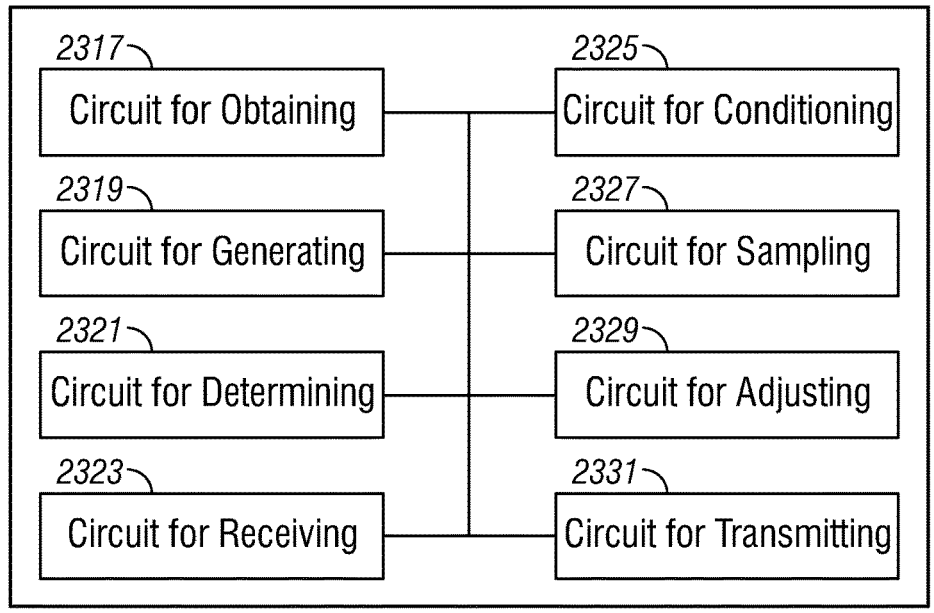
FIG. 23 is a block diagram of another apparatus in accordance with certain aspects of the present disclosure.

FIG. 23 illustrates aspects of a wireless communication device 2315. The wireless communication device may correspond to a sensor such as the sensor 501 of FIG. 5. In one aspect, the wireless communication device 2315 comprises a circuit for receiving 2323, a circuit for adjusting 2329, a circuit for generating 2319, a circuit for transmitting 2331, a circuit for obtaining 2317, a circuit for determining 2321, a circuit for conditioning 2325, and a circuit for sampling 2327. The circuit for receiving 2323 may correspond to the BAN Radio 514 of FIG. 5 of the BAN Radio 514 in conjunction with the BAN MAC 516. The circuit for adjusting 2329 may correspond to the processing system 505. The circuit for generating 2319 may correspond to the CS ADC 513 of FIG. 5 or to the CS ADC 513 in conjunction with the BAN MAC 516 and the processing system 505 of FIG. 5. The circuit for transmitting 2331 may correspond to the BAN Radio 514 of FIG. 5 or to the BAN Radio 514 in conjunction with the BAN MAC 516 of FIG. 5. The circuit for obtaining 2317 may correspond to the LNA 511 of FIG. 5 or to the LNA 511 in conjunction with the DAC 508. The circuit for determining 2321 may correspond to the LNA 511 and CS ADC 513 of FIG. 5. The circuit for conditioning 2325 may correspond to the LNA 511 and CS ADC 513 of FIG. 5. The circuit for sampling 2327 may correspond to the CS ADC circuit 513 of FIG. 5.

The various operations of methods described above may be performed by any suitable means capable of performing the corresponding functions. The means may include various hardware and/or software component(s) and/or module(s), including, but not limited to a circuit, an application specific integrate circuit (ASIC), or processor.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, a plurality of DSP cores, one or more microprocessors in conjunction with one or more DSP cores, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM, a signal, and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, a signal, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by an access terminal and/or access point as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that an access terminal and/or access point can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

A wireless device in the present disclosure may include various components that perform functions based on signals that are transmitted by or received at the wireless device. A wireless device may also refer to a wearable wireless device. In some aspects the wearable wireless device may comprise a wireless headset or a wireless watch. For example, a wireless headset may include a transducer adapted to provide audio output based on data received via a receiver. A wireless watch may include a user interface adapted to provide an indication based on data received via a receiver. A wireless sensing device may include a sensor adapted to provide data to be transmitted via a transmitter.

A wireless device may communicate via one or more wireless communication links that are based on or otherwise support any suitable wireless communication technology. For example, in some aspects a wireless device may associate with a network. In some aspects the network may comprise a personal area network (e.g., supporting a wireless coverage area on the order of 30 meters) or a body area network (e.g., supporting a wireless coverage area on the order of 10 meters) implemented using ultra-wideband technology or some other suitable technology. In some aspects the network may comprise a local area network or a wide area network. A wireless device may support or otherwise use one or more of a variety of wireless communication technologies, protocols, or standards such as, for example, CDMA, TDMA, OFDM, OFDMA, WiMAX, and Wi-Fi. Similarly, a wireless device may support or otherwise use one or more of a variety of corresponding modulation or multiplexing schemes. A wireless device may thus include appropriate components (e.g., air interfaces) to establish and communicate via one or more wireless communication links using the above or other wireless communication technologies. For example, a device may comprise a wireless transceiver with associated transmitter and receiver components (e.g., transmitter 210 or 302 and receiver 212 or 304) that may include various components (e.g., signal generators and signal processors) that facilitate communication over a wireless medium.

The teachings herein may be incorporated into (e g, implemented within or performed by) a variety of apparatuses (e.g., devices). For example, one or more aspects taught herein may be incorporated into a phone (e.g., a cellular phone), a personal data assistant ("PDA") or so-called smartphone, an entertainment device (e.g., a portable media device, including music and video players), a headset (e.g., headphones, an earpiece, etc.), a microphone, a medical sensing device (e.g., a biometric sensor, a heart rate monitor, a pedometer, an EKG device, a smart bandage, etc.), a user I/O device (e.g., a watch, a remote control, a light switch, a keyboard, a mouse, etc.), an environment sensing device (e.g., a tire pressure monitor), a monitoring device that may receive data from the medical or environment sensing device (e.g., a desktop, a mobile computer, etc.), a point-of-care device, a hearing aid, a set-top box, or any other suitable device. The monitoring device may also have access to data from different sensing devices via connection with a network.

These devices may have different power and data requirements. In some aspects, the teachings herein may be adapted for use in low power applications (e.g., through the use of an impulse-based signaling scheme and low duty cycle modes) and may support a variety of data rates including relatively high data rates (e.g., through the use of high-bandwidth pulses).

In some aspects a wireless device may comprise an access device (e.g., an access point) for a communication system. Such an access device may provide, for example, connectivity to another network (e.g., a wide area network such as the Internet or a cellular network) via a wired or wireless communication link. Accordingly, the access device may enable another device (e.g., a wireless station) to access the other network or some other functionality. In addition, it should be appreciated that one or both of the devices may be portable or, in some cases, relatively non-portable. Also, it should be appreciated that a wireless device also may be capable of transmitting and/or receiving information in a non-wireless manner (e.g., via a wired connection) via an appropriate communication interface.

The invention claimed is:

1. A method of processing data, the method comprising:
maintaining, at a first apparatus, a first clock signal, wherein the first apparatus comprises a gateway of a body area network (BAN);
transmitting, from the first apparatus, a clock synchronization signal for synchronizing a second clock signal, at a second apparatus, to the first clock signal, wherein the second apparatus comprises a sensor in the BAN;
receiving, at the first apparatus, one or more packets comprising a first set of samples indicative of an input over a period of time, the first set of samples corresponding to the second clock signal, and wherein samples in the first set of samples are spaced at non-uniform time-instances over the period of time; and generating, at the first apparatus, a second set of samples representing the signal over the period of time based, at least in part, on the first set of samples, wherein the second set of samples corresponds to the first clock signal, and wherein samples in the second set of samples are spaced at uniform time instances over the period of time.

2. The method of claim 1, wherein the first set of samples comprises $k+\delta$ samples, wherein k is a target number of samples and $\delta$ is a number of additional or absent samples.

3. The method of claim 2, further comprising:
determining a mismatch amount to which the first and second clock signals are not synchronized, wherein in the number of additional or absent samples is based, at least in part, on the mismatch amount; and
comparing the mismatch amount to a threshold, wherein:
the clock synchronization signal is transmitted when the mismatch amount the amount exceeds the threshold.

4. The method of claim 1, wherein the clock synchronization signal is transmitted periodically or aperiodically.

5. The method of claim 1, wherein:
the first set of samples comprises n samples, wherein n is less than a number of samples corresponding to Nyquist rate sampling the signal over the period of time; and
the second set of samples comprises n samples, wherein n is greater than or equal to a number of samples corresponding to Nyquist rate sampling the signal over the period of time.

6. The method of claim 1, further comprising:
receiving a third set of samples, wherein the third set of samples corresponds to a third clock signal, wherein the third set of samples represents a second signal over the period of time, and wherein samples in the third set of samples are spaced at non-uniform time instances over the period of time; and
generating a fourth set of samples representing the second signal over the period of time based, at least in part, on the third set of samples, the fourth set of samples corresponding to the second clock signal, and wherein samples in the fourth set of samples are spaced at uniform time instances over the period of time.

7. A gateway of a body area network (BAN), comprising:
means for maintaining a first clock signal;
means for transmitting a clock synchronization signal for synchronizing a second clock signal, at a sensor in the BAN, to the first clock signal;
means for receiving one or more packets comprising a first set of samples indicative of an input over a period of time, the first set of samples corresponding to the second clock signal, and wherein samples in the first set of samples are spaced at non-uniform time-instances over the period of time; and
means for generating, at the gateway of the BAN, a second set of samples representing the signal over the period of time based, at least in part, on the first set of samples, wherein the second set of samples corresponds to the first clock signal, and wherein samples in the second set of samples are spaced at uniform time instances over the period of time.

8. The gateway of claim 7, wherein the first set of samples comprises $k+\delta$ samples, wherein k is a target number of samples and $\delta$ is a number of additional or absent samples.

9. The gateway of claim 8, further comprising:
means for determining a mismatch amount to which the first and second clock signals are not synchronized, wherein in the number of additional or absent samples is based, at least in part, on the mismatch amount; and
means for comparing the mismatch amount to a threshold, wherein:
the clock synchronization signal is transmitted when the mismatch amount the amount exceeds the threshold.

10. The gateway of claim 7, wherein the clock synchronization signal is transmitted periodically or aperiodically.

11. The gateway of claim 7, wherein:
the first set of samples comprises n samples, wherein n is less than a number of samples corresponding to Nyquist rate sampling the signal over the period of time; and
the second set of samples comprises n samples, wherein n is greater than or equal to a number of samples corresponding to Nyquist rate sampling the signal over the period of time.

12. The gateway of claim 7, further comprising:
means for receiving a third set of samples, wherein the third set of samples corresponds to a third clock signal, wherein the third set of samples represents a second signal over the period of time, and wherein samples in the third set of samples are spaced at non-uniform time instances over the period of time; and
means for generating a fourth set of samples representing the second signal over the period of time based, at least in part, on the third set of samples, the fourth set of samples corresponding to the second clock signal, and wherein samples in the fourth set of samples are spaced at uniform time instances over the period of time.

13. A gateway of a body area network (BAN), comprising:
at least one processor coupled with a memory and configured to maintain a first clock signal;
a transmitter configured to transmit a clock synchronization signal for synchronizing a second clock signal, at a sensor in the BAN, to the first clock signal; and
a receiver configured to receive one or more packets comprising a first set of samples indicative of an input over a period of time, the first set of samples corresponding to the second clock signal, wherein:
samples in the first set of samples are spaced at non-uniform time-instances over the period of time;
the at least one processor is further configured to generate a second set of samples representing the signal over the period of time based, at least in part, on the first set of samples;
the second set of samples corresponds to the first clock signal; and
samples in the second set of samples are spaced at uniform time instances over the period of time.

14. The gateway of claim 13, wherein the first set of samples comprises $k+\delta$ samples, wherein k is a target number of samples and $\delta$ is a number of additional or absent samples.

15. The gateway of claim 14, wherein:
the at least one processor is further configured to:
determine a mismatch amount to which the first and second clock signals are not synchronized, wherein in the number of additional or absent samples is based, at least in part, on the mismatch amount; and
compare the mismatch amount to a threshold; and the transmitter is configured to transmit the clock synchronization signal when the mismatch amount the amount exceeds the threshold.

16. The gateway of claim 13, wherein transmitter is configured to transmit the clock synchronization signal periodically or aperiodically.

17. The gateway of claim 13, wherein:
the first set of samples comprises n samples, wherein n is less than a number of samples corresponding to Nyquist rate sampling the signal over the period of time; and
the second set of samples comprises n samples, wherein n is greater than or equal to a number of samples corresponding to Nyquist rate sampling the signal over the period of time.

18. The gateway of claim 13, wherein:
the receiver is further configured to receive a third set of samples, the third set of samples corresponding to a third clock signal, the third set of samples representing a second signal over the period of time, and the third set of samples being spaced at non-uniform time instances over the period of time; and
the at least one processor is further configured to generate a fourth set of samples representing the second signal over the period of time based, at least in part, on the third set of samples, the fourth set of samples corresponding to the second clock signal, and samples in the fourth set of samples being spaced at uniform time instances over the period of time.

* * * * *